(12) United States Patent
Timmons et al.

(10) Patent No.: US 10,067,090 B2
(45) Date of Patent: Sep. 4, 2018

(54) SYSTEM AND METHOD FOR CHARACTERIZING FERROMAGNETIC MATERIAL

(71) Applicant: The Charles Stark Draper Laboratory, Inc., Cambridge, MA (US)

(72) Inventors: Brian P. Timmons, Milford, MA (US); Rami S. Mangoubi, Newton, MA (US); Zachary R. Hoffman, Boston, MA (US); Franklyn R. Webb, Revere, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 15/653,036

(22) Filed: Jul. 18, 2017

(65) Prior Publication Data

US 2017/0315094 A1    Nov. 2, 2017

Related U.S. Application Data

(63) Continuation of application No. 15/197,699, filed on Jun. 29, 2016.

(Continued)

(51) Int. Cl.
*G01R 19/00* (2006.01)
*G01N 27/83* (2006.01)
*G01N 33/20* (2006.01)

(52) U.S. Cl.
CPC ............ *G01N 27/83* (2013.01); *G01N 33/20* (2013.01)

(58) Field of Classification Search
CPC ................. G01N 27/83; G01N 33/20

(Continued)

(56) References Cited

U.S. PATENT DOCUMENTS

| 3,379,970 A | 4/1968 | Kusenberger et al. |
| 4,292,589 A | 9/1981 | Bonner |

(Continued)

FOREIGN PATENT DOCUMENTS

| EP | 2 808 677 A1 | 12/2014 |
| RU | 2 264 617 C2 | 11/2005 |

(Continued)

OTHER PUBLICATIONS

Ahmad, et al., "A Survey of Low Duty Cycle MAC Protocols in Wireless Sensor Networks," Emerging Communications for Wireless Sensor Networks, InTech Open, 23 pages, Feb. 2011.

(Continued)

*Primary Examiner* — Stephanie Bloss
(74) *Attorney, Agent, or Firm* — Sunstein Kann Murphy & Timbers LLP

(57) ABSTRACT

A system and method using magnetic sensing to non-intrusively and non-destructively characterize ferromagnetic material within infrastructure. The system includes sensors for measuring magnetic field gradients from a standoff distance adjacent to ferromagnetic material. The method includes using the system to measure magnetic fields, determining magnetic field gradients measured by a sensor array, and comparing measured and modeled or historical magnetic field gradients at the same or similar positions to identify differences caused by a phenomenon in the ferromagnetic material, and, in a particular embodiment, to recognize defects and developing defects.

37 Claims, 17 Drawing Sheets

Related U.S. Application Data

(60) Provisional application No. 62/185,888, filed on Jun. 29, 2015, provisional application No. 62/265,851, filed on Dec. 10, 2015.

(58) Field of Classification Search
USPC .......................................................... 702/64
See application file for complete search history.

(56) References Cited

U.S. PATENT DOCUMENTS

| | | | |
|---|---|---|---|
| 4,309,659 A | 1/1982 | Yoshii | |
| 4,492,115 A | 1/1985 | Kahil et al. | |
| 4,538,108 A | 8/1985 | Huschelrath et al. | |
| 4,710,712 A | 12/1987 | Bradfield et al. | |
| 4,930,026 A | 5/1990 | Kljuev et al. | |
| 5,614,825 A | 3/1997 | Maxfield et al. | |
| 5,675,252 A | 10/1997 | Podney | |
| 5,777,477 A | 7/1998 | Wynn | |
| 6,205,859 B1 | 3/2001 | Kwun et al. | |
| 6,243,657 B1 * | 6/2001 | Tuck | G01N 29/2412 324/207.13 |
| 6,320,820 B1 | 11/2001 | Gardner et al. | |
| 6,476,610 B1 | 11/2002 | Wiegert et al. | |
| 6,483,302 B1 | 11/2002 | Rusnell et al. | |
| 6,809,516 B1 | 10/2004 | Li et al. | |
| 7,145,330 B2 | 12/2006 | Xiao | |
| 7,155,369 B2 | 12/2006 | Papadimitriou et al. | |
| 7,161,351 B2 | 1/2007 | Goldfine et al. | |
| 7,259,556 B2 | 8/2007 | Popovic et al. | |
| 7,423,931 B2 | 9/2008 | Martin, II et al. | |
| 7,652,572 B2 * | 1/2010 | Roybal | G01V 3/081 324/260 |
| 7,835,226 B2 | 11/2010 | Kokosalakis et al. | |
| 7,944,165 B1 | 5/2011 | O'Dell | |
| 8,060,835 B2 | 11/2011 | Newcomer et al. | |
| 8,104,349 B2 | 1/2012 | Kubota et al. | |
| 8,214,161 B2 | 7/2012 | Girndt | |
| 8,390,283 B2 | 3/2013 | Mather et al. | |
| 8,447,532 B1 | 5/2013 | Goroshevskiy et al. | |
| 8,542,127 B1 | 9/2013 | Goroshevskiy et al. | |
| 8,949,042 B1 | 2/2015 | Goroshevskiy et al. | |
| 9,513,258 B2 * | 12/2016 | Freear | G01N 27/82 |
| 9,651,471 B2 | 5/2017 | Davis et al. | |
| 9,651,472 B2 | 5/2017 | Davis et al. | |
| 2002/0116980 A1 | 8/2002 | Kerr et al. | |
| 2007/0069720 A1 | 3/2007 | Goldfine et al. | |
| 2007/0115821 A1 | 5/2007 | Sim et al. | |
| 2008/0031213 A1 | 2/2008 | Kaiser et al. | |
| 2009/0319551 A1 | 12/2009 | Jung et al. | |
| 2010/0030491 A1 * | 2/2010 | Ziegel | F17D 5/00 702/34 |
| 2010/0321009 A1 * | 12/2010 | Lee | G01M 5/0033 324/209 |
| 2012/0123699 A1 | 5/2012 | Kawata et al. | |
| 2012/0253696 A1 * | 10/2012 | Pearson | G01N 27/82 702/38 |
| 2013/0024135 A1 | 1/2013 | Blum | |
| 2013/0027029 A1 | 1/2013 | Goroshevskiy et al. | |
| 2013/0128786 A1 | 5/2013 | Sultan et al. | |
| 2014/0293850 A1 | 10/2014 | Huang et al. | |
| 2014/0336937 A1 | 11/2014 | Hallundbaek | |
| 2015/0042323 A1 | 2/2015 | Freear et al. | |
| 2015/0046582 A1 | 2/2015 | Gelvin et al. | |
| 2015/0149103 A1 | 5/2015 | Shimizu | |
| 2015/0330946 A1 | 11/2015 | Davis et al. | |
| 2016/0323839 A1 | 11/2016 | Davis et al. | |
| 2017/0108469 A1 | 4/2017 | Timmons et al. | |

FOREIGN PATENT DOCUMENTS

| | | |
|---|---|---|
| WO | WO 2009/097427 A1 | 8/2009 |
| WO | WO 2013/019136 A1 | 2/2013 |
| WO | WO 2013/128210 A1 | 9/2013 |
| WO | WO 2015/179237 A1 | 11/2015 |

OTHER PUBLICATIONS

Basu, et al., "Effect of Overhearing Transmissions on Energy Efficiency in Dense Sensor Networks," IPSN'04, 9 pages, Apr. 26-27, 2004.

De, et al., "ActSee: Activity-Aware Radio Duty-Cycling for Sensor Networks in Smart Environments," Department of Computer Science, Georgia State University, 8 pages, 2011.

Desai, et al., "Robust Gaussian and Non-Gaussian Matched Subspace Detection," IEEE Transactions on Signal Processing, vol. 51, No. 12, Dec. 2003.

Du, et al., "RMAC: A Routing-Enhanced Duty-Cycle MAC Protocol for Wireless Sensor Networks," Department of Computer Science, Rice University, pp. 1478-1486, 2007.

Dunkels, "The ContikiMAC Radio Duty Cycling Protocol," SICS Technical Report, T2011:13, ISSN 1100-3154, pp. 1-11, Dec. 2011.

Hashemi, et al., "Intra-Car Multihop Wireless Sensor Networking: A Case Study," Automotive Networking and Applications, IEEE Communications Magazine, vol. 52, No. 12, pp. 183-191, Dec. 2014.

Ilyas, et al., "Handbook of Sensor Networks: Compact Wireless and Wired Sensing Systems," CRC Press, 3 pages, 2005.

Jawhar, et al., "Ferry-Based Linear Wireless Sensor Networks," College of Information Technology, UAE University, pp. 1-6, 2013.

Jawhar, et al., "Linear wireless sensor networks: Classification and applications," Journal of Network and Computer Applications, vol. 34, pp. 1671-1682, 2011.

Jin, et al., "Monitoring of Distributed Pipeline Systems by Wireless Sensor Networks," Proceedings of the 2008 IAJC-IJME International Conference, 10 pages, 2008.

Karl, et al., "Protocols and Architectures for Wireless Sensor Networks," John Wiley & Sons, 5 pages, Oct. 8, 2007.

Leone, "Radio duty cycling," https://github.com/contikios/contiki/wiki/Radio-duty-cycling, 7 pages, Jul. 29, 2014.

Ludovici, et al., "Forwarding Techniques for IP Fragmented Packets in a Real 6LoWPAN Network," Sensors, vol. 11, pp. 992-1008, Jan. 18, 2011.

Mohamed, et al., "Sensor Network Architectures for Monitoring Underwater Pipelines," Sensors, vol. 11, pp. 10738-10764, Nov. 15, 2011.

Pasadas, et al., "Handheld Instrument to Detect Defects in Conductive Plates with a Planar Probe," 2011 IEEE International Instrumentation and Measurement Technology Conference, 6 pages, May 2011.

Rohrback Cosasco System, Inc., "Cosasco® Wireless Best Practices: A Guide for Planning, Installation, and Commissioning," Rohrback Cosasco Systems, Inc., Bulletin No. AN-119, 8 pages, May 11, 2011.

Rohrback Cosasco Systems, Inc., "Quicksand™ Erosion Detection System," Rohrback Cosasco Systems, Inc., Bulletin No. 700-J, 3 pages, Mar. 15, 2012.

Rohrback Cosasco Systems, Inc., "Quicksand™ Wireless Transmitter MWT-3905-QS," Rohrback Cosasco Systems, Inc., Bulletin No. 160-G, 6 pages, Jun. 27, 2012.

Sadeghioon, et al., "SmartPipes: Smart Wireless Sensor Networks for Leak Detection in Water Pipelines," Journal of Sensor and Actuator Networks, vol. 3, pp. 64-78, Feb. 20, 2014.

Tiporlini, et al., "High Sensitivity Optically Pumped Quantum Magnetometer," The Scientific World Journal, vol. 2013, Article ID 858379, 8 pages, May 2013.

Valliappan, "Wireless: What is clear channel assessment (CCA)?," Quora, http://www.quora.com/Wireless/What-is-clear-channel-assessment-CCA, 2 pages, Mar. 7, 2013.

Weiss, et al., "The importance of low power sensing for the Internet of Things," Dust Networks Product Group, Linear Technology Corp., 4 pages, Oct. 5, 2013.

Xu, et al., "On Localized Prediction for Power Efficient Object Tracking in Sensor Networks," Distributed Computing Systems Workshops, Proceedings, 23rd International Conference, pp. 434-439, May 2003.

Zimmerling, et al., "Energy-Efficient Routing in Linear Wireless Sensor Networks," IEEE Xplore, 3 pages, 2007.

(56) References Cited

OTHER PUBLICATIONS

Wikipedia, Ad hoc On-Demand Distance Vector Routing, Wikipedia, http://en.wikipedia.org/wiki/Ad_hoc_On-Demand_Distance_Vector_Routing, 3 pages, Aug. 7, 2014.
Wikipedia, Energy harvesting, Wikipedia, http://en.wikipedia.org/w/index.php?title=Energy_Harvesting&oldid=607544418, 10 pages, May 7, 2014.
Wikipedia, 6LoWPAN, Wikipedia, http://en.wikipedia.org/wiki/6LoWPAN, 4 pages, Aug. 20, 2014.
Wikipedia, Magnetostriction, Wikipedia, http://en.wikipedia.org/wiki/Magnetostriction, 2 pages, May 8, 2014.
Wikipedia, Mesh networking, Wikipedia, http://en.wikipedia.org/wiki/Mesh_networking, 6 pages, Sep. 19, 2014.
Wikipedia, Wireless sensor network, Wikipedia, https://en.wikipedia.org/w/index.php?title=Wireless_sensor_network&oldid=606602738, 8 pages, May 1, 2014.
European Patent Office, ISA, International Search Report—International Application No. PCT/US2015/031092, dated Aug. 27, 2015, together with the Written Opinion of the International Searching Authority, 11 pages.
Korean Intellectual Property Office, ISA, International Search Report—International Application No. PCT/US2016/014241, dated Apr. 15, 2016, together with the Written Opinion of the International Searching Authority, 14 pages.
US Commissioner for Patent, ISA, International Search Report, International Application No. PCT/US16/40211, dated Mar. 17, 2017, together with the Written Opinion of the International Searching Authority, 16 pages.

* cited by examiner

SYSTEM AND METHOD FOR CHARACTERIZING FERROMAGNETIC MATERIAL

CROSS-REFERENCE TO RELATED APPLICATIONS

This application is a continuation of U.S. patent application Ser. No. 15/197,699, filed Jun. 29, 2016, entitled "System and Method for Characterizing ferromagnetic Material," which claims the benefit of U.S. Provisional Patent Application No. 62/185,888, filed Jun. 29, 2015, entitled "Detection of Defects in Ferromagnetic Materials using Large Standoff Magnetization (LSM) Sensors," and U.S. Provisional Patent Application No. 62/265,851, filed Dec. 10, 2015, entitled "System and Method for Characterizing Ferromagnetic Material," each of which is hereby incorporated by reference herewith, in its entirety, for all purposes.

BACKGROUND ART

Metal components of structures are susceptible to defects, such as due to imperfect manufacture, corrosion, fatigue, wear, damage, etc. To prevent catastrophic failure of such structures, metal components may be visually inspected to identify defects before a failure occurs. However, many structures are not easily inspected due to being buried underground or beneath the sea, or due to being embedded within other materials such as concrete. For large infrastructure that contains metal components, visual inspection may be impractical or too costly to perform routinely.

Many ferromagnetic objects, including steel pipe, act as weak permanent magnets even when not intentionally magnetized; for example, magnetic dipoles in steel may partially orient to the Earth's magnetic field after cooling below the Curie temperature when cast or hot-rolled in the foundry. Magnetic fields present in ferromagnetic objects as stray byproducts of their manufacture are known herein as parasitic fields. The Earth's magnetic field also induces magnetic fields in ferromagnetic objects. These magnetic fields permit detection of ferromagnetic objects from a distance. Magnetic exploders for naval mines and torpedoes have been designed to detect magnetic fields from large ferrous objects, such as warships, since 1917, although both German and American magnetic exploders were problematic when used in combat on torpedoes in 1939-1943. Magnetic exploders, however, are merely intended to detect the object from a distance, not to detect or analyze defects in that object.

Magnetic particle inspection is well known as a method for detecting cracks in objects. In this technique, a ferromagnetic object is placed in a magnetic field, and magnetic particles, such as iron filings, are applied to the object. The magnetic field may be provided by passing an electric current through the object, or by placing the object in a field provided by an electromagnet. If a crack is present, the magnetic particles cluster near the crack. Field strengths used for magnetic particle inspection are typically much greater than the Earth's magnetic field, or those parasitic fields that may be present in ferromagnetic materials.

SUMMARY OF EMBODIMENTS

According to an embodiment, a method for characterizing a ferromagnetic material includes: receiving measured magnetic field data from a plurality of sensors adjacent the ferromagnetic material at a plurality of locations along the ferromagnetic material; deriving measured magnetic field features from the measured magnetic field data; comparing the derived magnetic field features with modeled or previously collected, verified magnetic field features to identify differences caused by a phenomenon in the ferromagnetic material.

According to another embodiment, a system for characterizing a ferromagnetic material includes: memory capable of storing magnetic field data from at least one sensor configured to measure magnetic field data at a plurality of scan positions along the ferromagnetic material, and software including machine readable instructions. The system may further include a processor coupled with the memory, the processor configured to, in response to execution of the software, perform the steps of: derive magnetic field feature data from the magnetic field data at the plurality of scan positions, and compare the measured magnetic field features data with modeled magnetic field feature data to identify a phenomenon in the ferromagnetic material.

BRIEF DESCRIPTION OF THE SEVERAL VIEWS OF THE DRAWING

The invention will be more fully understood by referring to the following Detailed Description of Specific Embodiments in conjunction with the Drawings, of which.

DETAILED DESCRIPTION OF SPECIFIC EMBODIMENTS

Figure 1:
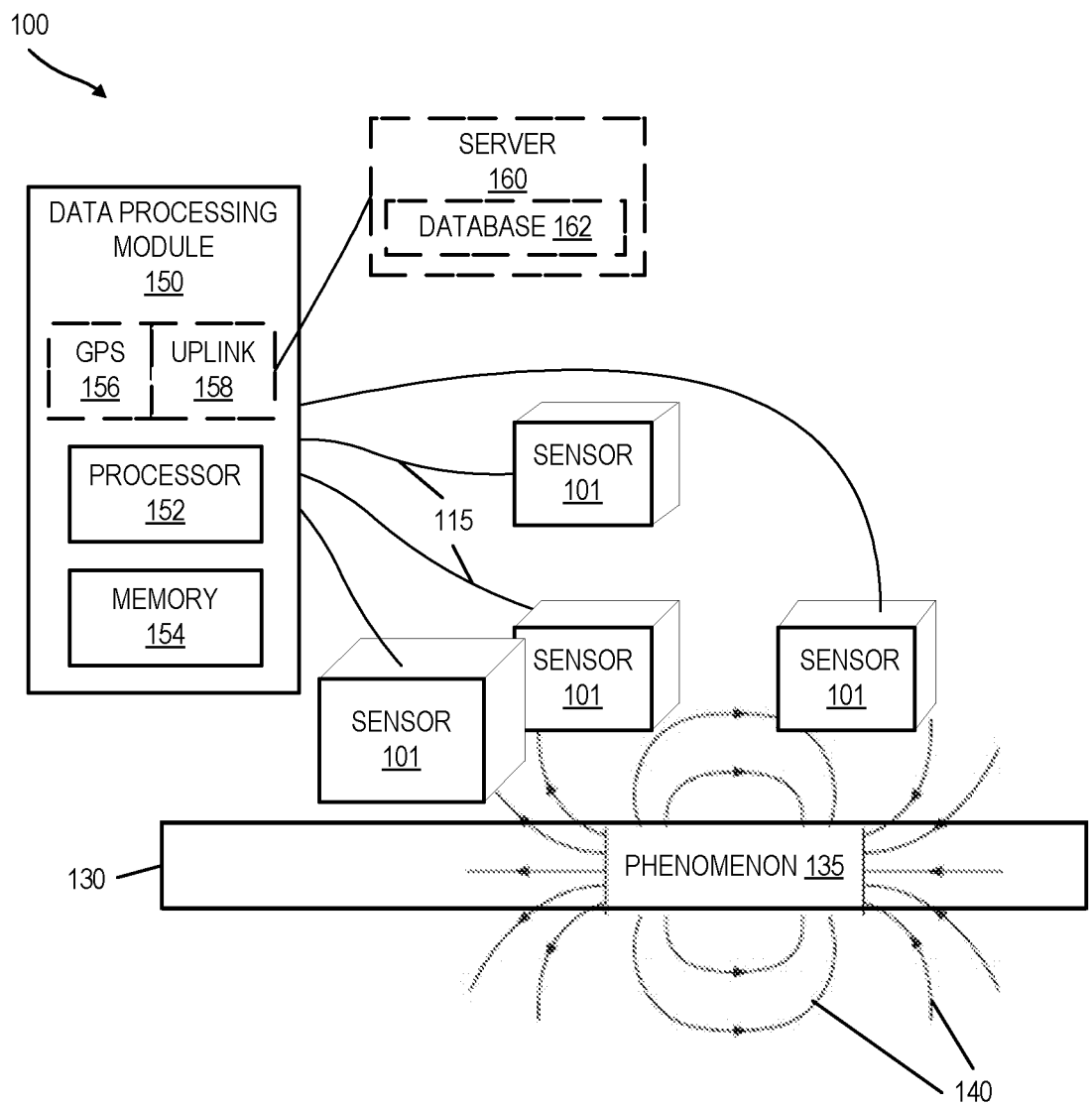
FIG. 1 is a block diagram of one system for characterizing ferromagnetic material, in an embodiment.

FIG. 1 schematically illustrates one system 100 for characterizing a ferromagnetic material 130, in embodiments. System 100 non-intrusively and non-destructively detects local phenomena in an infrastructure, including defects and non-defects, based on ferromagnetic material 130. System 100 includes a plurality of magnetic sensors 101. Although FIG. 1 shows four magnetic sensors 101, system 100 may have more or fewer sensors 101 without departing from the scope hereof. Sensors 101 couple to a data processing module 150 via communication paths 115, which may include one or both of a wired and/or a wireless communication media. Data processing module 150 processes magnetic field measurements received from sensors 101 via communication paths 115 to characterize ferromagnetic material 130 as described below. Data processing module 150 has at least one processor 152 coupled with a memory 154, and may in some embodiments have a global positioning system (GPS) receiver 156 and/or a digital-radio uplink 158. Digital-radio uplink 158 may operate through a cell phone network, or other wireless network such as WiFi, for example, to transmit or receive information to a server 160. Server 160 may include, in embodiments, a database 162 of anomalies.

Ferromagnetic material 130 exhibits magnetization based on its structure, composition, and fabrication history. At the same time, ferromagnetic material 130 may have a phenomenon 135 that perturbs the magnetic field from ferromagnetic material 130, as illustrated by magnetic field lines 140 in FIG. 1, wherein phenomenon 135 "disrupts" an otherwise spatially regular magnetic field of ferromagnetic material 130. Phenomenon 135 is for example (a) a weld or junction between segments of ferromagnetic material 130, (b) an unintentional irregularity of cracked, missing or otherwise faulty ferromagnetic material (hereinafter called a "defect" and typically due to corrosion, fatigue, wear, damage or imperfect manufacture; some defects may lead to infrastructure failure), or (c) an intentionally-designed gap or opening. Sensors 101 may be magnetometers arranged in an array to measure magnetic field 140 related to phenomenon 135.

Identifying a defect in material 130 prior to failure in components such as reinforcing steel, pipelines, oil platform legs, ship hulls, etcetera buried underground or located underwater often requires inspecting beneath a visible surface. The embodiments disclosed herein may be suitable in evaluating ferromagnetic material of such infrastructure including, but not limited to: industrial vessels and pipes of plants and equipment, including power plants, refineries and heat exchangers; pipelines, such as oil and gas pipelines; railways, including rails and bridges of railroads, light-rail and subways; structures, such as buildings and bridges made with ferrous beams or rebar-reinforced concrete; and partially or fully submerged drilling rigs, ships and submarines.

During use of system 100 to inspect infrastructure, system 100 is positioned near, and moved along ferromagnetic material 130 while system 100 measures material-associated magnetic field 140. Sensors 101 are arranged in a spatially distributed array that provides a spatial map of magnetic field 140, at each traveled location along material 130, with each sensor 101 measuring both magnetic direction and magnitude. Data processing module 150 in turn processes magnetic field measurements received from the array of sensors 101 via communication paths 115 to characterize magnetic field 140, thereby providing a current scan of magnetic field along ferromagnetic material 130.

In data processing system 150, processor 152 may execute software (for example software 263 discussed in further detail below with respect to FIG. 2), realized as machine readable instructions stored in memory 154, to implement (a) scan routines to store the current scan of the magnetic field in memory 152, and (b) analysis routines to analyze the scan of the magnetic field for anomalies such as phenomenon 135. If an anomaly is located, processor 152 may further execute additional software (for example software 263 discussed in further detail below), also realized as machine readable instructions stored in memory 154, to implement further analysis routines on the stored scan to identify the anomaly as a non-defect, such as a weld, flange, or intentionally-designed gap/opening, or identify the anomaly as a defect, such as a missing metal defect or other unintentional fault within the material 130. It should be appreciated that various aspects of data processing system 150 may be performed remotely, such as in server 160, without departing from the scope hereof. For example, the analysis routines, including analyzing the scan of magnetic field for anomalies such as phenomenon 135, may be performed on a scan that is previously implemented by data processing module 150 (via scan routines) and then transmitted from data processing module 150 to server 160.

In embodiments, the analysis routines operate by determining signature phenomena, of the observed magnetic field (such as phenomena in, or functions of, the magnetic field gradients and derivatives thereof) as recorded from multiple locations in a sliding window of the scan. In an embodiment, the software (for example software 263 discussed in further detail below) implementing such analysis routines determines signature phenomena by fitting a superposition of predefined signature phenomena. The predefined signature phenomena may be derived from (a) computer models of magnetic dipoles to the observed magnetic field from the locations in the sliding window, (b) a non-dipole based model, (c) measurements, or (d) a combination thereof.

Information about anomaly types, including classifications of the anomaly types and pattern phenomena corresponding to each anomaly type, may be stored in memory 154 and/or database 162. In an embodiment optimized for analysis of pipelines, the anomaly types include exemplary good welds and exemplary defective welds, as well as cracks, breaks, valves, taps, and corroded locations. The analysis routines may be configured to provide the classification that most closely matches each anomaly found during a scan.

A location read from GPS 156, and/or other location sensors such as an odometer, may in some embodiments be associated with a portion of the scan associated with a defect, or in some embodiments portions of the scan associated with a non-defect, such as a weld or flange, and these locations and associated scan windows are reported through uplink 158 to server 160 and stored in database 162. Since weld locations in a pipeline, or bolted joints in railroad track, are unlikely to change with time in infrastructure 130, new phenomena, or phenomena that have significantly changed character since any prior scan, can indicate incipient failure such as cracks in a pipe or breaks in rail. Either processor 152 or server 160, may correlate the current and prior scan to align phenomena, and then compare phenomena of anomalies detected in the current scan to observations made during a prior scan at the same location, as may have been previously recorded in database 162, to determine whether the phenomenon is new, and identify it as new. New phenomena, as well as phenomena classified as defects, may warrant further investigation, such as by excavating a pipeline.

In particular embodiments, system 100 does not include a bias magnet for magnetizing the ferromagnetic material 130. In these embodiments, the magnetic fields sensed by system 100 are parasitic magnetic fields and fields induced in the ferromagnetic material by the Earth's magnetic field.

Figure 2:
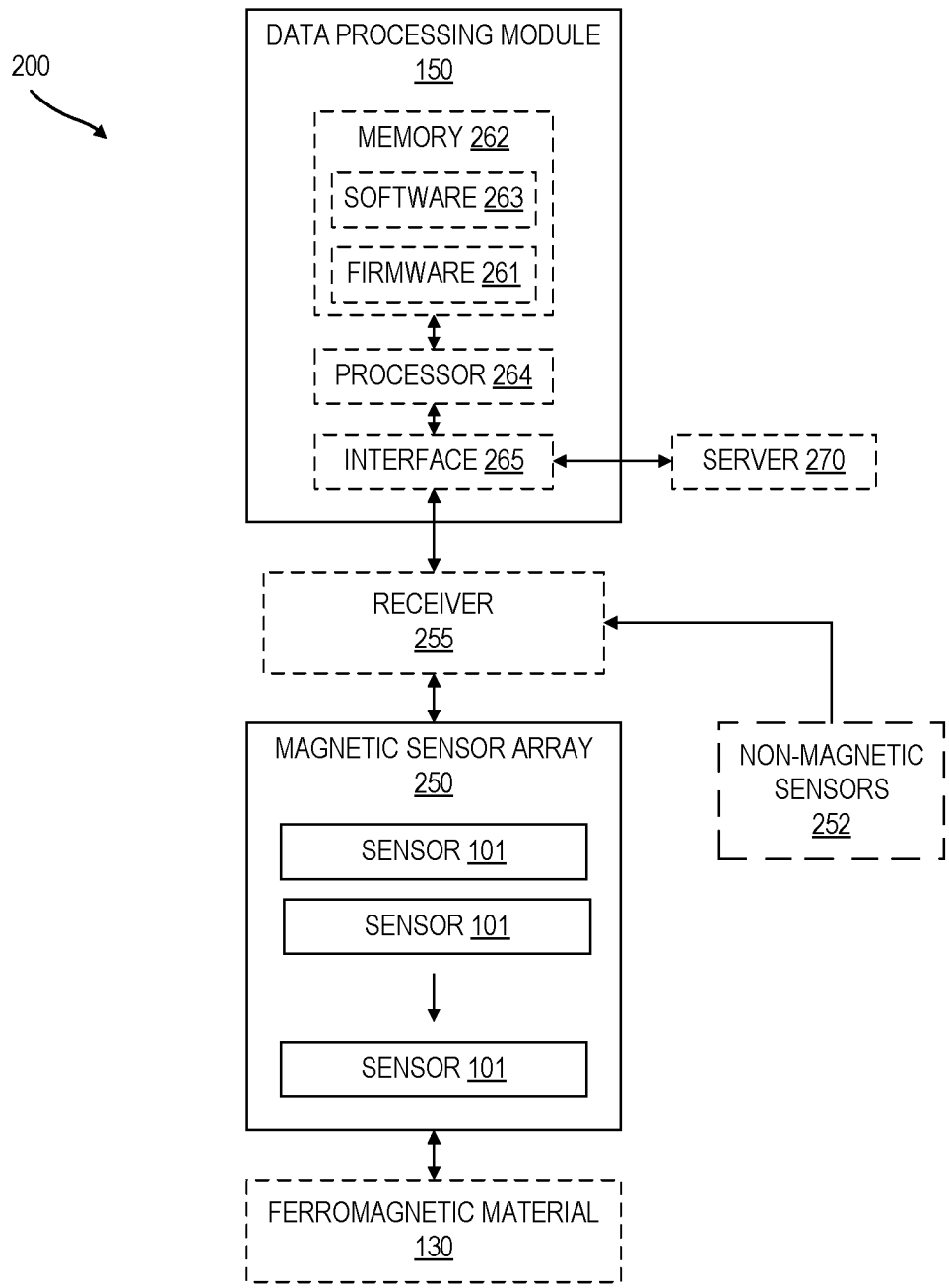
FIG. 2 is a block diagram of another system for characterizing ferromagnetic material, in an embodiment.

FIG. 2 schematically illustrates a system 200 that characterizes ferromagnetic material. System 200 is a an embodiment of system 100 In system 200, sensors 101, of FIG. 1, are implemented in a sensor array 250 that communicatively couples to data processing module 150. System 200 implements data processing module 150 with at least one processor 264 in communication with memory 262. Processor 264 is an embodiment of processor 152. Memory 262 is an embodiment of memory 154 and may be transitory and/or non-transitory and in some embodiments includes one or both of (a) volatile memory such as RAM and (b) non-volatile memory such as, ROM, EEPROM, Flash-EEPROM, magnetic media including disk drives, optical media. Memory 262 stores software 263 and firmware 261 as machine readable instructions executable by processor 264 to process data from sensor array 250 and identify and/or characterize one or more phenomena 135 of ferromagnetic material 130. It should be appreciated that various aspects of software 263 and firmware 261 may be implemented by server 160 shown in FIG. 1, instead of, or in addition to, data processing module 150. In embodiments, measurements from sensor array 250 are received by a receiver 255 that communicates measurements to data processing module 150. In other embodiments, measurements are communicated directly from sensor array 250 to data processing module 150. Receiver 255 is for example a data acquisition device. In embodiments, data from non-magnetic sensors 252 (e.g., accelerometers) are also received by receiver 255, as more fully described below. Illustratively, data processing module 150 includes an interface 265 for communicating with other devices, including server 270 that processes and stores data. Server 270 is similar to server 160, and therefore the discussion of server 160 applies equally to server 270. Although data processing module 150 is shown as a single device, it should be appreciated that data processing module 150 may incorporate one or more devices such as computers, processors, memories, etc.

Figure 3:
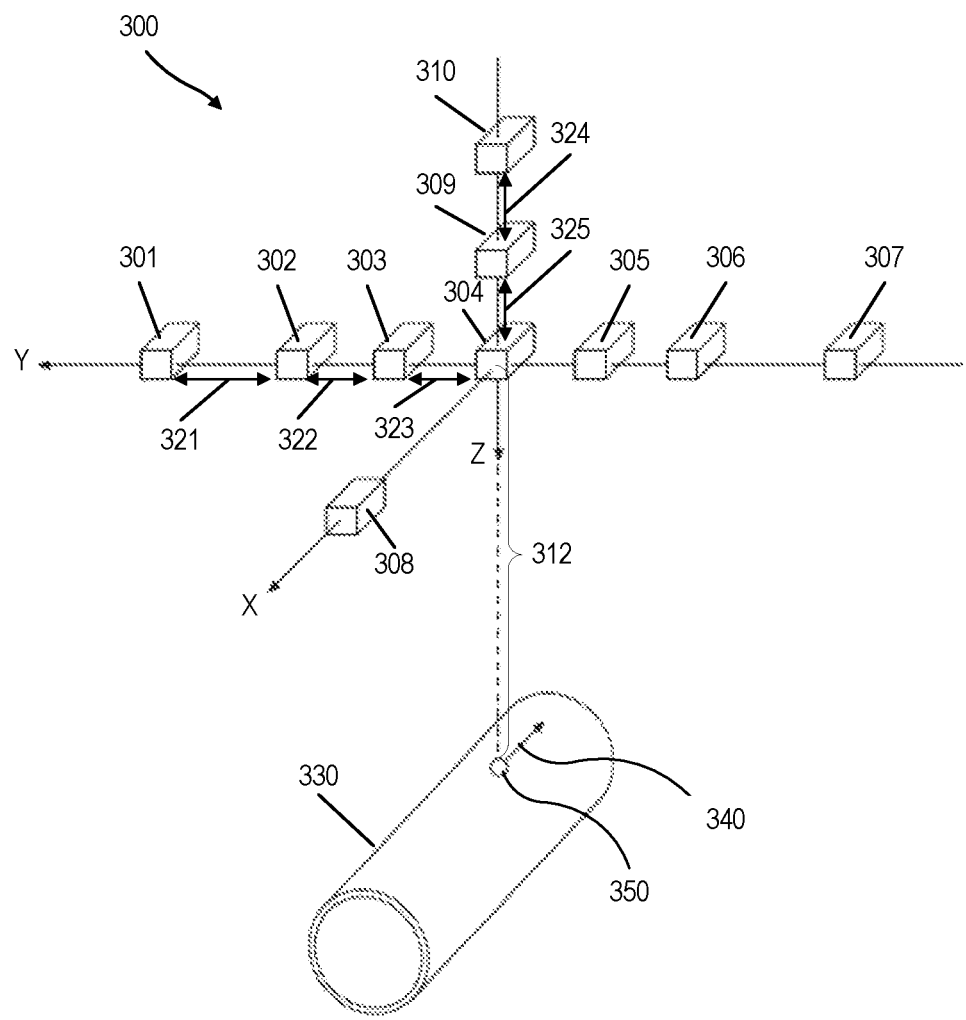
FIG. 3 illustrates one magnetic sensor array used in a system for characterizing ferromagnetic material, in an embodiment.

FIG. 3 schematically illustrates an exemplary magnetic sensor array 300 for characterizing ferromagnetic material 330 in the form of a pipe. Sensor array 300 includes ten magnetic sensors, including a first magnetic sensor 301, a magnetic second sensor 302, and so on up to a tenth magnetic sensor 310 arranged in a three-dimensional (3D) array. More or fewer magnetic sensors may be utilized without departing from the scope hereof. Sensor array 300 is an embodiment of sensor array 250, FIG. 2, and each sensor 301-310 is for example an embodiment of sensor 101 of FIGS. 1-2. FIG. 3 illustrates an exemplary "T" arrangement of sensors 301-310 positioned along three orthogonally oriented axes.

Although in FIG. 3, sensor array 300 is shown in a "T" arrangement, the sensor array 300 may be configured in other patterns without departing from the scope hereof. For example, sensor array 300 may also be implemented in non-orthogonal arrangements, instead of the orthogonal arrangement shown in FIG. 3 without departing from the scope hereof. Moreover, sensor array 300, in either a non-orthogonal or an orthogonal arrangement may be configured with more or fewer magnetic sensors, and could be deployed in positions and arranged in a pattern, such as in a cone- or sphere-shaped pattern. Furthermore, in embodiments, the sensor array may be synthesized with just a single magnetic sensor moved between known positions to make multiple measurements as a data array. Likewise, the locations of sensors 301-310 need not be restricted to locations along the axes of a 3D coordinate system. One- or two-dimensional arrays may also be beneficially employed as array 300.

Magnetic sensor array 300 is positioned with a standoff distance 312 above ferromagnetic material 330 having a defect 350. Ferromagnetic material 330 is an example of ferromagnetic material 130, FIG. 1, while defect 350 is an example of phenomenon 135. Defect 350 is for example a missing metal defect, a corrosion-induced defect, or any other type of irregularity that is substantially different from an expected shape and structure of ferromagnetic material 330. Defect 350 thus causes a magnetic field phenomenon with an exemplary magnetization direction indicated by arrow 340. Standoff distance 312 may be known, estimated or measured, for example using ground penetrating radar.

The ability to sense magnetic fields with sensor arrays, such as sensor array 300, depends on standoff distance 312, the strength of magnetic field 340 from ferromagnetic material 330, the sensitivity of magnetic sensors 301-310, and spacing distances 321, 322, 323, 324, 325 between sensors 301-310 in sensor array 300. In an embodiment, magnetic sensors 301-310 are magnetometers that measure magnetic fields. Magnetic sensors 301-310 may be one-axis magnetometers that measure magnetic fields along one axis, two-axis magnetometers that measure magnetic fields along two axes, or three-axis magnetometers that measure magnetic fields along three axes. The three axes are for example x, y, and z axes depicted in FIG. 3. Note that sensor array 300 includes variable spacing distances between magnetic sensors 301-310; for example, a first distance 321 between magnetic sensors 301 and 302 is greater than a second distance 322 between magnetic sensors 302 and 303. Similarly along the z-axis, a fourth distance 324 may be greater than a fifth distance 325. In an embodiment, first, second, third, fourth, and fifth distances 321, 322, 323, 324, 325 are optimized to measure dipole magnetic fields and determine magnetic field gradient peak signatures of defect 350 for a given standoff distance 312. In an operational example, which the embodiments herein are not limited to, a third distance 323 between magnetic sensors 303 and 304 is about 15 cm for a standoff distance 312 of 25 cm. In another operational example, magnetic sensors 301-310 have adjustable positions within sensor array 300 such that sensor spacing distances 321, 322, 323, 324, 325 are adjusted to optimize measurement of magnetic fields having different field strengths for different standoff distances 312.

Figure 4:
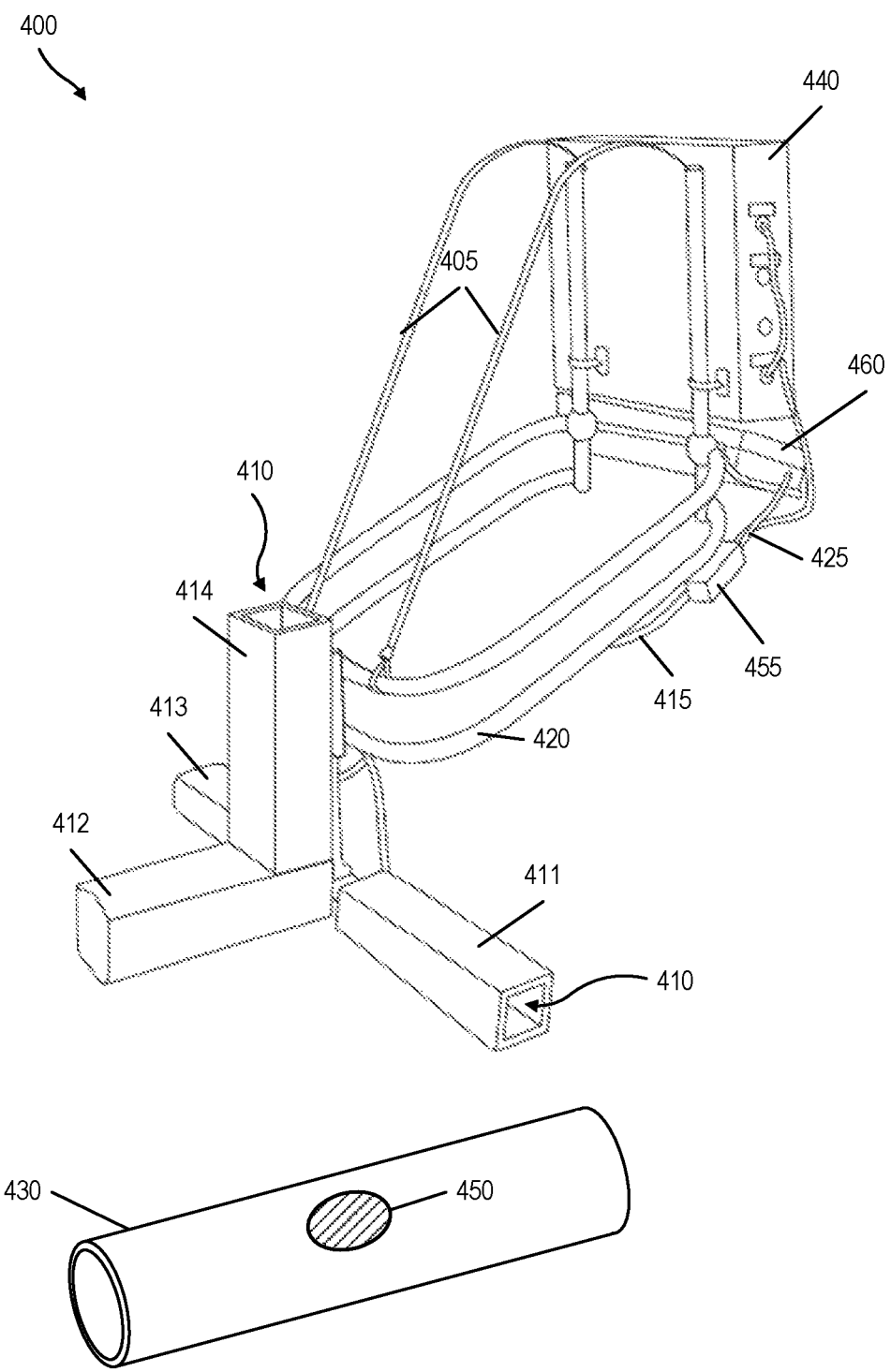
FIG. 4 illustrates a system for characterizing ferromagnetic material, in an embodiment.

FIG. 4 illustrates yet another system 400 for characterizing ferromagnetic material 430. System 400 is an embodiment of system 100. System 400 shows four sensor arms 411, 412, 413, 414 each of which contains one or more sensors 410 (e.g., magnetometers) that measure magnetic field strength. Sensors 410 may be arranged in an array, such as the sensor array 300 of FIG. 3, and attached to a frame 420 by sensor arms 411, 412, 413, 414 or by other structure when moving the array of sensors 410 along ferromagnetic material 430. Sensors 410 are an embodiment of sensors 101 and are arranged in an example of sensor array 250. Ferromagnetic material 430 is an example of ferromagnetic material 130. By way of example, frame 420 may be equipped with straps 405 or other means for a user to carry system 400. In another embodiment, system 400 is mechanically coupled to a vehicle, such as an automobile, train, aerial vehicle, or underwater vehicle. Sensor arms 411, 412, 413, 414 may be moveable up and down along frame 420 to account for variation in standoff distance 312.

A power supply 440 electrically couples to sensors 410 to provide direct current (DC) electrical power. Power supply 440 may be wired to an electrical grid or have a battery pack that enables remote, off-grid use of system 400. A receiver 455 couples to sensors 410 via communication path 415, which is similar to communication path 115 of FIG. 1, to receive data therefrom. Receiver 455 is for example an embodiment of receiver 255, FIG. 2. A computer 460 connects to receiver 455 via communication path 425 to process received sensor data. Computer 460 is for example an embodiment of data processing module 150 implementing processor(s) 264, memory 262, and optional interface 265. Communication paths 415, 425 may include one or both of a wired and/or a wireless communication media.

Figure 5:
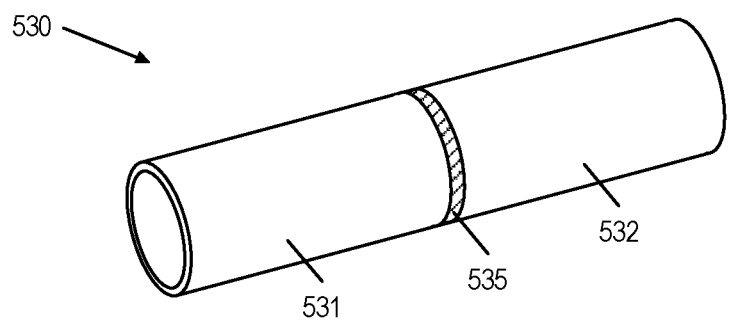
FIG. 5 illustrates a pipe made of ferromagnetic material.

FIG. 5 shows an exemplary pipe 530 made of ferromagnetic material. Pipe 530 is an example of ferromagnetic material 130 and 430 and may be characterized using any of systems 100, 200, and 400. Pipe 530 includes a weld 535, which is a welded junction that joins a first segment 531 to a second segment 532 of pipe 530. Weld 535 is an example of an intentional non-defect phenomenon that produces a characteristic magnetic field phenomenon providing a magnetic field signature that may resemble a magnetic dipole. For example, magnetic flux leakage may occur at weld 535 producing the magnetic field signature. In an embodiment, magnetic field signatures are determined in real-time and used for calibration and compensation of magnetic field measurements caused by variability such as platform motion or standoff distance 312. Data processing module 150 compares magnetic field measurements obtained by sensors 101 to known magnetic field signatures to detect a defect, such as defect 450, FIG. 4. In FIG. 2, memory 262 may thus include at least one magnetic field signature for this purpose.

Figure 6:
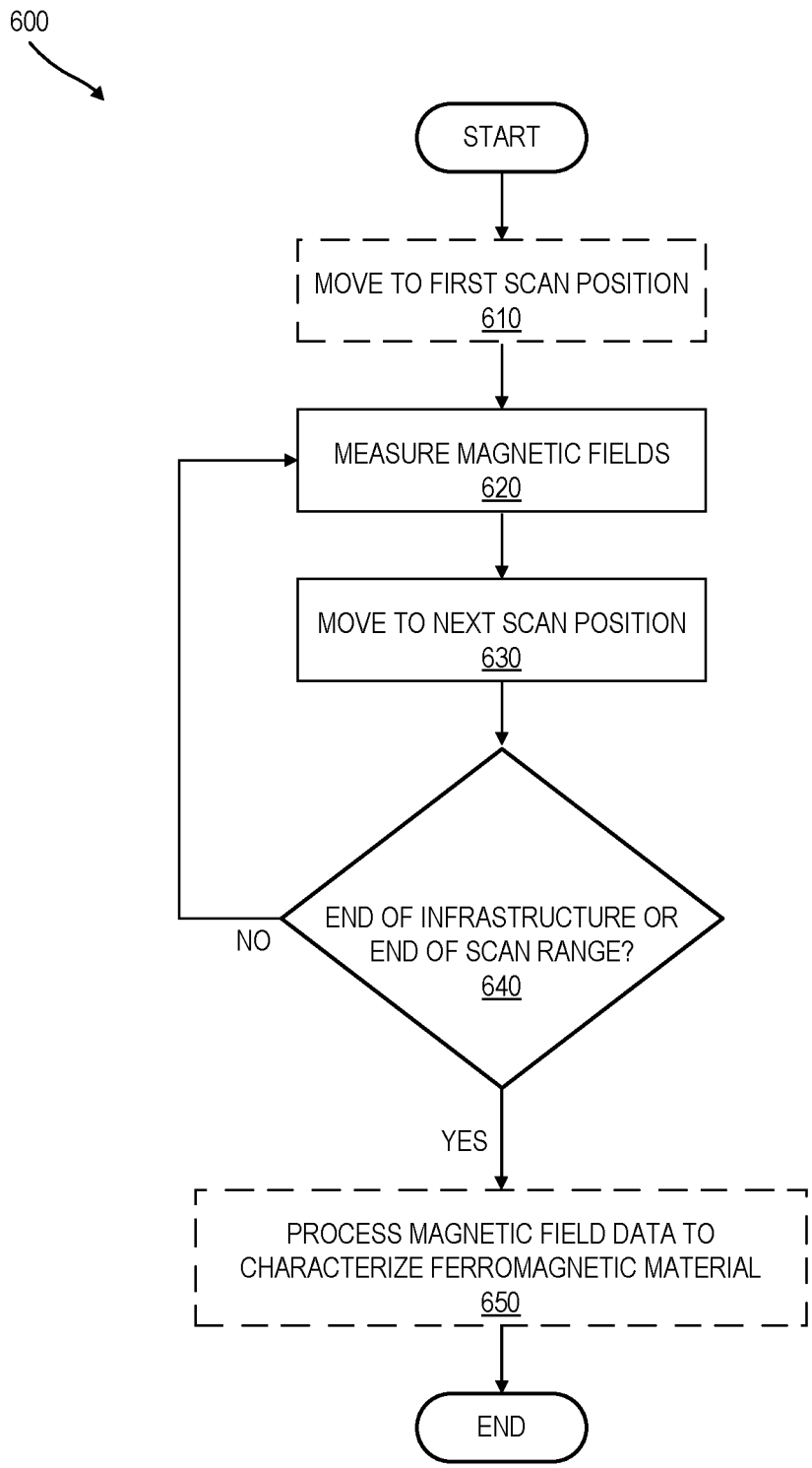
FIG. 6 is a flowchart including steps of a method to characterize ferromagnetic material, in an embodiment.

FIG. 6 is a flowchart illustrating steps of an exemplary method 600 for measuring magnetic field 140 from infrastructure containing ferromagnetic material 130. Method 600 is an example of a "scan routine" as discussed above with respect to FIGS. 1, 2, and 4. As such, method 600 may be performed by system 100 of FIG. 1, system 200 of FIG. 2, and system 400 of FIG. 4, for example using data processing module 150 executing software 263.

In an optional step 610, the system for characterizing ferromagnetic material moves to a first scan position, such as an arbitrary location adjacent to infrastructure containing ferromagnetic material. In an example of step 610, system 400 of FIG. 4 is moved to a position adjacent to first segment 531 of pipe 530 of FIG. 5. In other examples, system 100 or 200, of FIGS. 1 and 2, is moved to a position adjacent to a first segment of ferromagnetic material 130.

In a step 620, the system measures magnetic fields. In an example of step 620, sensors 410 measure a magnetic field (e.g. magnetic field 140) from first segment 531. In other examples of step 620, sensors 110 of FIGS. 1-2, possibly in the arrangement of array 300 of FIG. 3, measure a magnetic field from ferromagnetic material 130.

In a step 630, the system for characterizing ferromagnetic material moves to a next scan position. In an example of step 630, system 400 of FIG. 4 moves to a position adjacent weld 535 of pipe 530 of FIG. 5. In another example of step 630, system 100 or 200, of FIG. 1-2, is moved to a next scan position along ferromagnetic material 130.

Step 640 is a decision. If in step 640 the end of the infrastructure is reached, or the end of a desired scan range is reached, method 600 ends. Otherwise, method 600 returns to step 620. In this way, method 600 is carried out to scan an entire infrastructure or a desired portion of an infrastructure. The rate at which magnetic fields are measured between first scan position and the next scan position may depend on bandwidth of data acquisition such as receiver 455 of FIG. 4. In an embodiment, system 400 is moved between locations at a rate of 0.25 meters per second. In another embodiment, system 100 or 200, of FIG. 1-2, is moved at a rate of 0.25 meters per second along ferromagnetic material 130.

Figure 7:
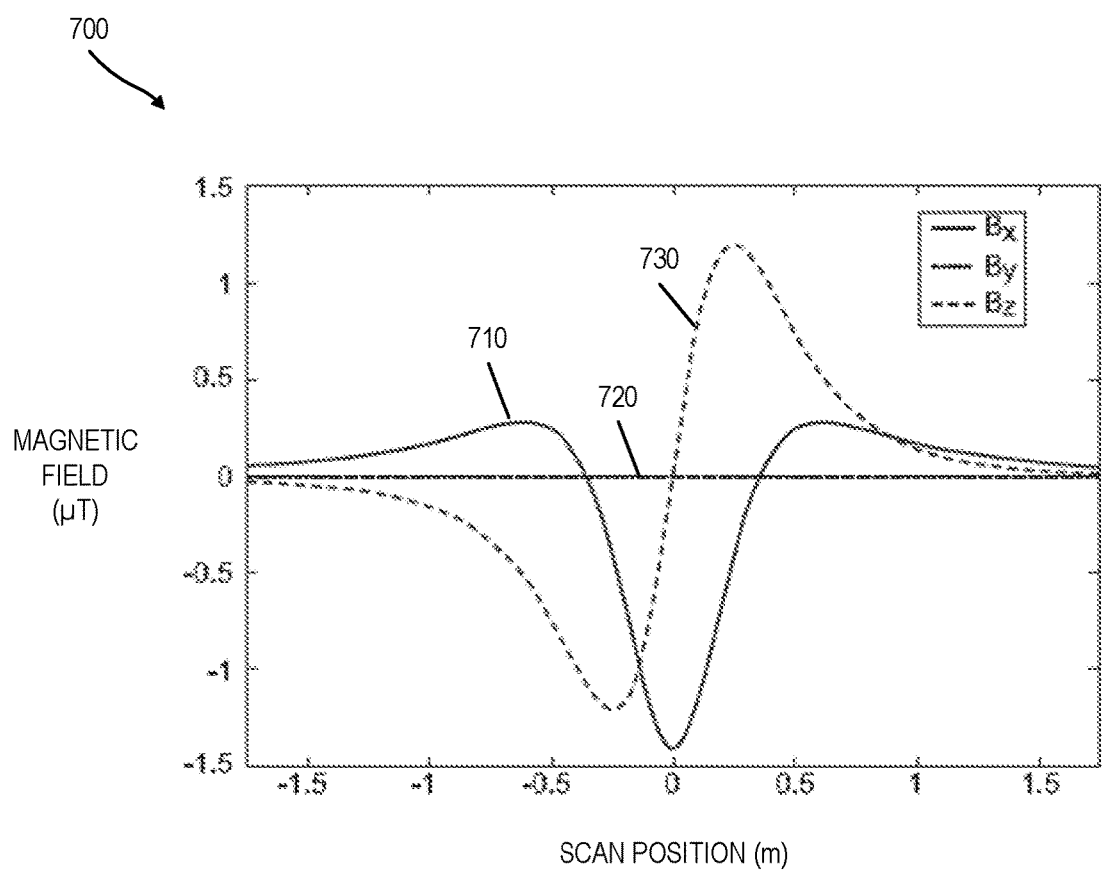
FIG. 7 shows a plot of magnetic field versus scan position from one sensor in a system that characterizes ferromagnetic material.

FIG. 7 shows a plot 700 of exemplary magnetic fields measured by one sensor, such as sensor 304 in array 300 or any of sensors 110 of FIGS. 1-2 and 410 of FIG. 4, versus scan position along pipe 330. Specifically, plot 700 illustrates exemplary magnetic field 140 measured by this sensor during method 600 over multiple iterations of step 620. Plot 700 includes magnitude of magnetic field, B, aligned in x, y, and z axes ($B_x$, $B_y$, $B_z$) versus scan position along pipe 330. A dataset 710 shows magnetic field strength along the x-axis, $B_x$, versus scan position; a dataset 720 shows magnetic field strength along the y-axis, $B_y$, versus scan position; and a dataset 730 shows magnetic field strength along the z-axis, $B_z$, versus scan position. The scan direction is oriented along the x-axis and sensor 304 is centered above pipe 330 in the y-dimension. By way of comparison, at a scan position of zero in FIG. 7, sensor 304 of FIG. 3 is positioned directly above defect 350. As sensor 304 is moved along ferromagnetic material 330, the scan position from defect 350 varies, corresponding to an increasing (positive values) or decreasing (negative values) scan position depending on the direction of movement.

Referring again to FIG. 6, in an optional step 650, magnetic field data measured from step 620 is processed to characterize ferromagnetic material 130. In an example of step 650, measured magnetic field data is compared, by data processing module 150 executing software 263 (or alternatively a remote server such as server 160 executing software similar to software 263), with an empirically determined or physics-based model of magnetic fields to identify and characterize phenomena in the magnetic field data caused by a phenomenon of ferromagnetic material 130. Measured data and modeled data are compared using for example matched filters or statistical-detection algorithms. One example of a physics-based model is a magnetic dipole model. Missing metal from ferromagnetic material produces predominantly magnetic dipole characteristics that are detected and matched with a magnetic dipole model. Missing metal defects, such as defect 350, FIG. 3, may have a dipole in reverse orientation to magnetization in ferromagnetic material 330. The reverse dipole orientation may be used to help identify defect 350. Similarly, welds forming junctions between segments of ferromagnetic material, such as weld 535 of FIG. 5, produce predominantly magnetic dipole characteristics. For example, at weld 535 between pipe segments 531, 532 dipoles may exist due to differences in magnetization direction and amplitude between pipe segments 531, 532 together with magnetic reorientation due to heating when the weld was made.

In a particular embodiment, modeled data is determined from a finite element model. In embodiments, model-based analysis, for example performed by data processing module 150 executing software 263, of magnetic dipoles detected by the system includes one or more of: applying interpolation on the magnetic field signature sphere to obtain the magnetic field at planes above and parallel and near-parallel to the pipe at different distances, and angles; extracting magnetic field spatial phenomena from the magnetic field, such as gradient, directional derivative, divergence or Laplacian, curl, magnitude and neighborhood local statistical moments of these phenomenon fields; obtaining daughter magnetic field phenomena from the field, such as a Spatial Fast-Fourier Transform (FFT) phase field, power spectral density (PSD), and Wavelet coefficients; separately analyzing each phenomenon statistically, for example using the t-test and the Wilcoxon Rank test; and selecting phenomena by collectively satisfying, or optimally satisfying, multiple criteria such as p-values, correlation to size and height, and orthogonality (non-correlation among phenomena). Nearby pairs and triplets of the above phenomena are fused for FFT and Wavelet analysis. Extracted phenomena are compared to a library of model-derived phenomena, such as welds and defects.

Figure 8:
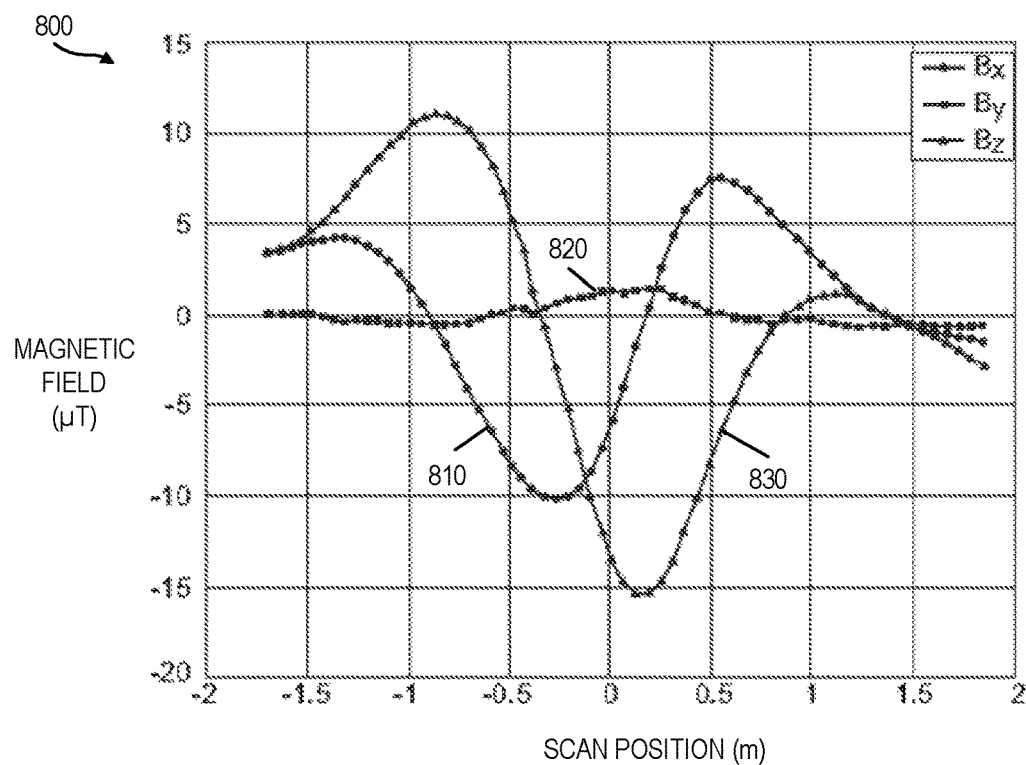
FIG. 8 illustrates a plot of measured magnetic field strength versus scan position for a system that characterizes ferromagnetic material.
Figure 9:
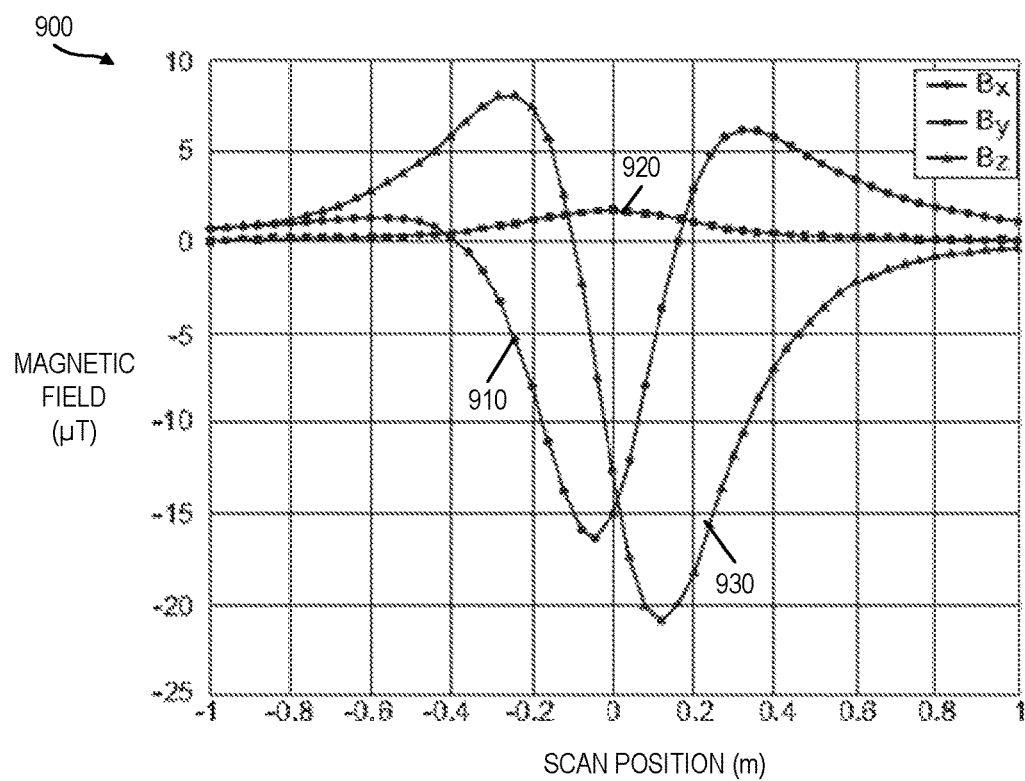
FIG. 9 illustrates a plot of dipole model magnetic field strength versus scan position for a system that characterizes ferromagnetic material.

FIGS. 8 and 9 show exemplary plots of measured and modeled magnetic field strength, respectively, as a function of scan position. FIG. 8 shows a plot 800 of exemplary magnetic fields measured by a single sensor (e.g. one of sensors of array 300) for a range of scan positions using method 600 of FIG. 6 implemented by system 400 of FIG. 4. Plot 800 may thus illustrate magnetic fields at a plurality of scan positions for weld 535 of FIG. 5 such as measured with sensor 304 for example. A dataset 810 shows magnetic field strength along the x-axis, $B_x$, a dataset 820 shows magnetic field strength along the y-axis, $B_y$, and a dataset 830 shows magnetic field strength along the z-axis, $B_z$, over a range of scan positions along the x-axis at a position centered over the pipe in the y-dimension. Magnetic field strength of pipe segments as determined at weld 535, such as that illustrated in plot 800, may be used for scaling magnetic field measurements from pipe segments 531, 532 to normalize data for improved detection of defects.

FIG. 9 shows a plot 900 of exemplary magnetic field strength versus scan position from a dipole model used in characterizing a ferromagnetic material phenomenon, such as weld 535 that joins first and second pipe segments 531, 532 of FIG. 5. A dataset 910 shows magnetic field strength along the x-axis, $B_x$, a dataset 920 shows magnetic field strength along the y-axis, $B_y$, and a dataset 930 shows magnetic field strength along the z-axis, $B_z$, versus scan position along the x-axis at a position centered over the pipe in the y-dimension.

According to an embodiment, data processing module 150 compares measured magnetic field plots, such as plot 800 of FIG. 8, with modeled magnetic field plots, such as plot 900 of FIG. 9 to distinguish a weld signature from a defect signature in step 650 of method 600, thereby detecting whether a defect has occurred. While both weld and defect signatures have dipole characteristics, magnetic field changes along the pipe may differ in magnitude from those expected at a weld. Further, field gradients at a weld will tend to taper from a field orientation in one segment of the pipe to a potentially-different orientation in another segment of the pipe, rather than returning to the same orientation beyond the defect as to be expected in a single section of pipe. This may be due to a broad transition zone between magnetic polarization of pipe sections produced as the metal was heated and cooled during welding, this transition zone being broader than typical missing metal defects.

Figure 9A:
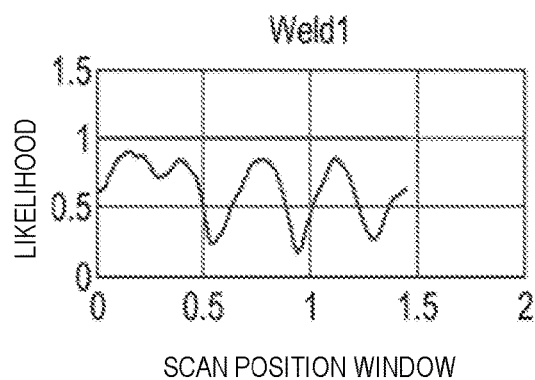
FIG. 9A and FIG. 9B represent plots of magnetic field gradients versus scan position in presence of a weld.
Figure 9B:
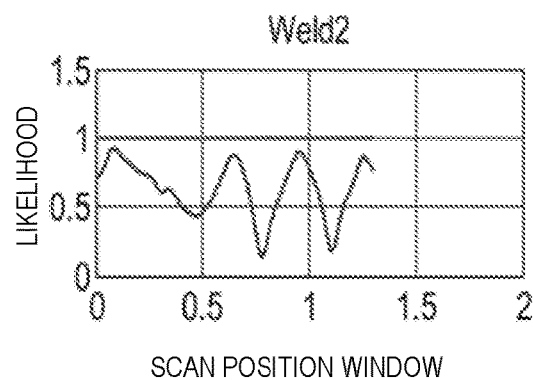

In an embodiment, a scalar likelihood, L, indicates the presence of a defect determined from gradients in all axes in a scan position window near the phenomenon, and from other statistical processing; if L is greater than a threshold, the phenomenon or anomaly is reported as a defect. FIGS. 9A-9D illustrate L plotted versus scan window position with a threshold of one; FIGS. 9A and 9B are associated with weld signatures and L<1 indicating non-defect, for FIGS. 9C and 9D, L>1 indicating a defect. The window size may be varied and the gradient data rescanned repeatedly with different window sizes depending on the sizes of ferromagnetic material, phenomenon (e.g. defects, weld, or anomaly) as discussed further below with respect to FIG. 18.

Magnetic fields calculated from dipole models for x, y and z-axes, such as those plotted versus scan position in FIG. 9, depend on orientation of the magnetic dipole. For example, a dipole may have an axial orientation along the scanning direction, for example along the x-axis of FIG. 3, a lateral orientation sideways from the scanning orientation, for example along the y-axis of FIG. 3, or a vertical orientation that is up and down from the scanning direction, for example along the z-axis of FIG. 3. A combination dipole has magnetization components of all three orientations, $C_x$, $C_y$, and $C_z$. Three-axis magnetic fields are calculated for a dipole model using Equation 1, below.

$$\begin{pmatrix} B_x \\ B_y \\ B_z \end{pmatrix} = \frac{1}{r^5} \begin{pmatrix} C_x(3x^2 - r^2) + 3C_y xy + 3C_z xz \\ 3C_x xy + C_y(3y^2 - r^2) + 3C_z yz \\ 3C_x xz + 3C_y yz + C_z(3z^2 - r^2) \end{pmatrix} \quad (1)$$

Equation 1 is the magnetic field equation for an arbitrary dipole orientation where $C_x$, $C_y$, and $C_z$ are combination magnetic fields proportional to magnetization along the x, y, and z-axes, respectively, and r is the absolute distance that includes standoff distance 312 from the sensor to the magnetic field source. In order for a magnetic signature to resemble a dipole, sensor distance from a magnetic source, r, is for example about two to three times longer than the magnetic source itself, although shorter sensor distances contain dipole characteristics that may be matched to Equation 1 if r is known.

Figure 10:
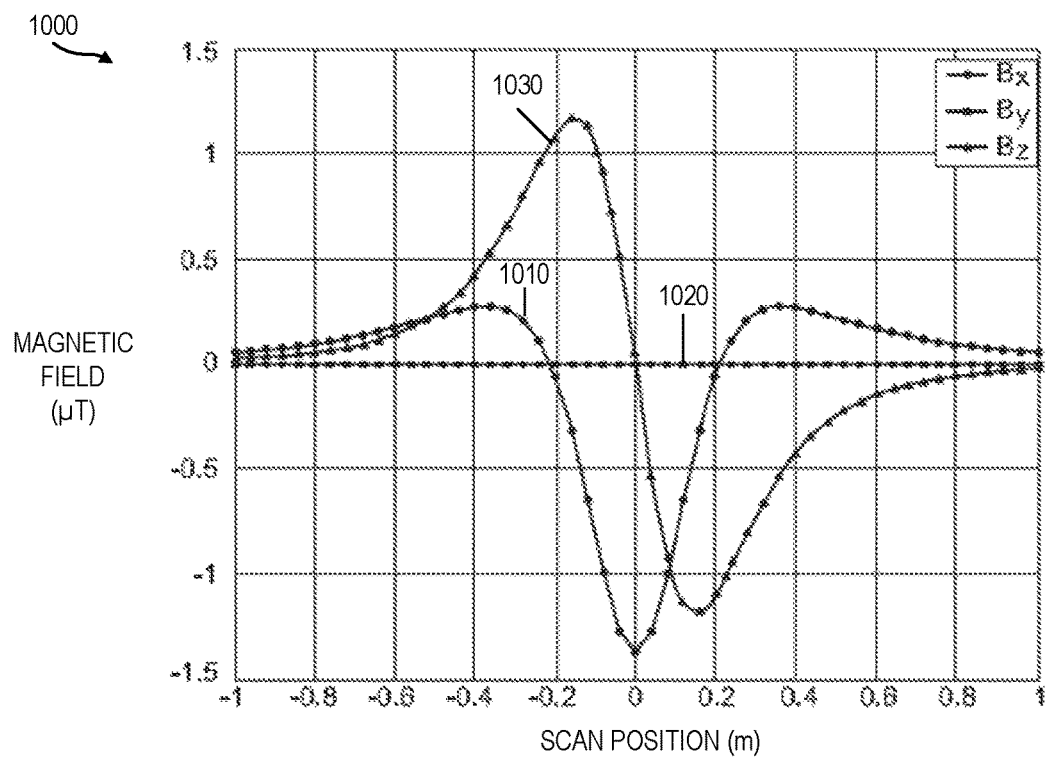
FIG. 10 shows a plot of magnetic field strength versus scan position for an axial dipole model, in an embodiment.

FIG. 10 shows a plot 1000 of exemplary modeled magnetic fields versus scan position for an axial dipole model, aligned with the x-axis, which may be used by data processing module 150 (or server 160 implementing analysis functions) to identify phenomena of ferromagnetic material 130. A dataset 1010 shows magnetic field strength along the x-axis, $B_x$, a dataset 1020 shows magnetic field strength along the y-axis, $B_y$, and a dataset 1030 shows magnetic field strength along the z-axis, $B_z$, for a magnetic dipole source oriented axially. $C_x$ is a constant, $C_y$ and $C_z$ are zero. Each of datasets 1010, 1020, and 1030 show the magnetic field as a function of x at a position centered over the magnetic dipole source in the y-direction.

Figure 11:
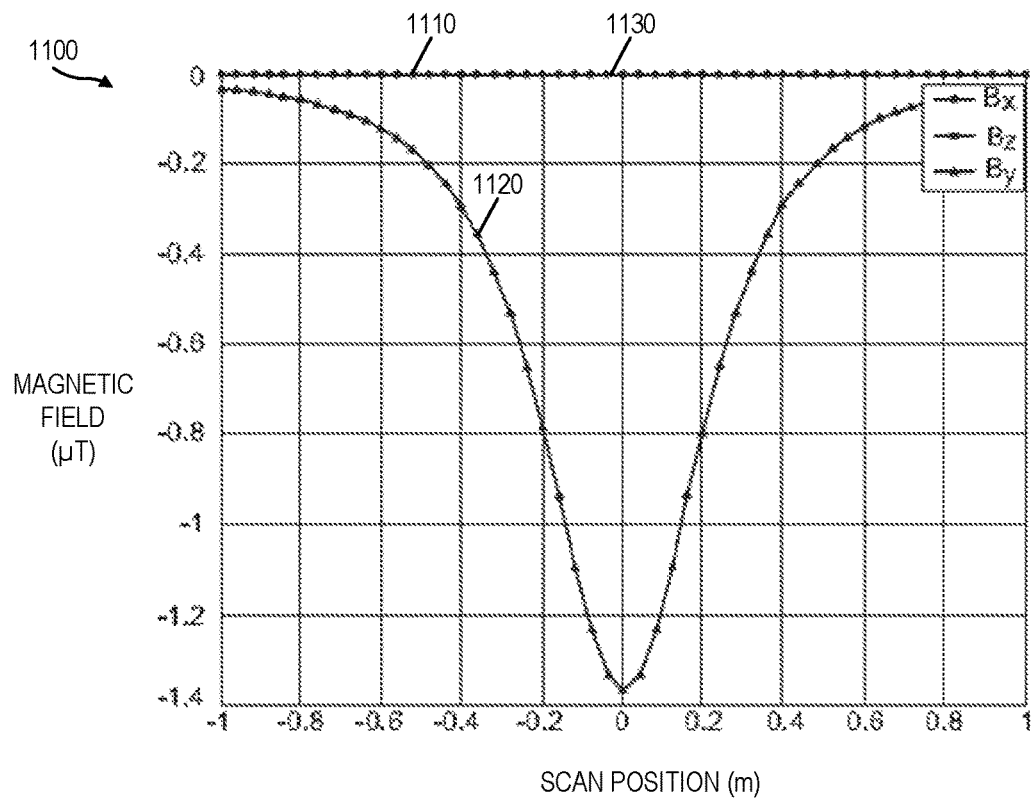
FIG. 11 shows a plot of magnetic field strength versus scan position for a lateral dipole model, in an embodiment.

FIG. 11 shows a plot 1100 of exemplary modeled magnetic field strength versus scan position for a lateral dipole model, aligned with the y-axis, which may be used by data processing module 150 (or server 160 implementing analysis functions) to identify phenomena of ferromagnetic material 130. A dataset 1110 shows magnetic field strength along the x-axis, $B_x$, a dataset 1120 shows magnetic field strength along the y-axis, $B_y$, and a dataset 1130 shows magnetic field strength along the z-axis, $B_z$ for magnetic dipole source oriented laterally. $C_y$ is a constant, $C_x$ and $C_z$ are zero. Each of datasets 1110, 1120, and 1130 show the magnetic field as a function of x at a position centered over the magnetic dipole source in the y-direction.

Figure 12:
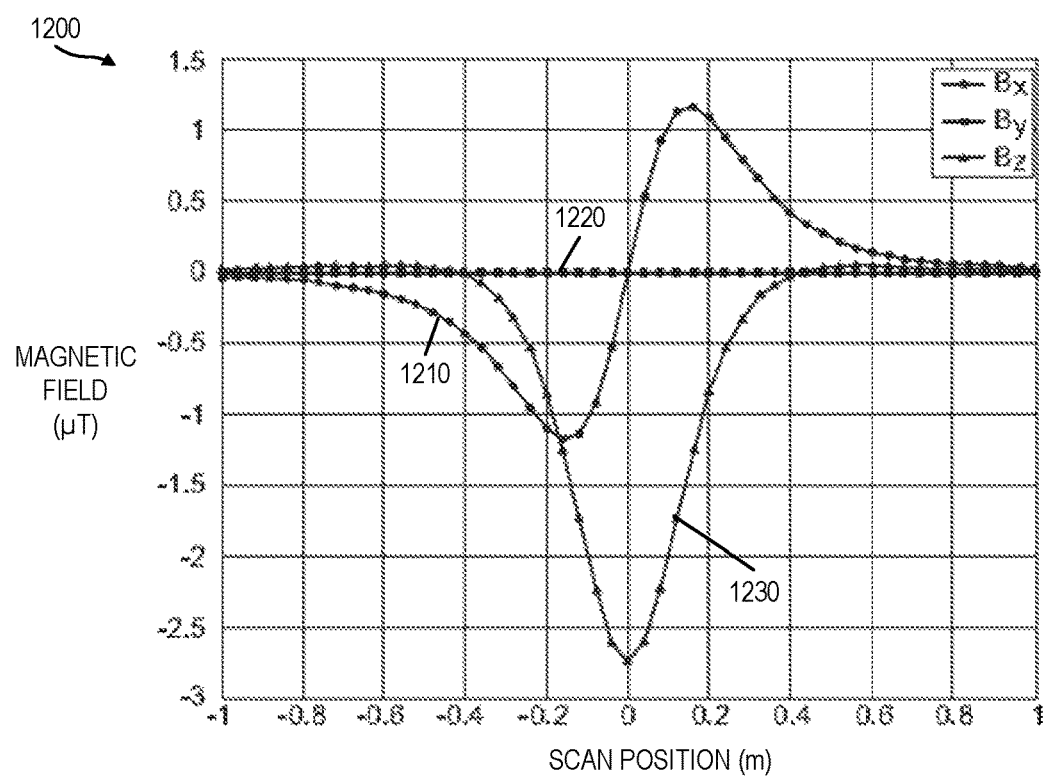
FIG. 12 shows a plot of magnetic field strength versus scan position for a vertical dipole model, in an embodiment.

FIG. 12 shows a plot 1200 of exemplary modeled magnetic field strength versus scan position for a vertical dipole model which may be used by data processing module to identify phenomena of ferromagnetic material 130. A dataset 1210 shows magnetic field strength along the x-axis, $B_x$, a dataset 1220 shows magnetic field strength along the y-axis, $B_y$, and a dataset 1230 shows magnetic field strength along the z-axis, $B_z$ for a magnetic dipole source oriented vertically. $C_z$ is a constant, $C_x$ and $C_y$ are zero. Each of datasets 1210, 1220, and 1230 show the magnetic field as a function of x at a position centered over the magnetic dipole source in the y-direction.

Figure 13:
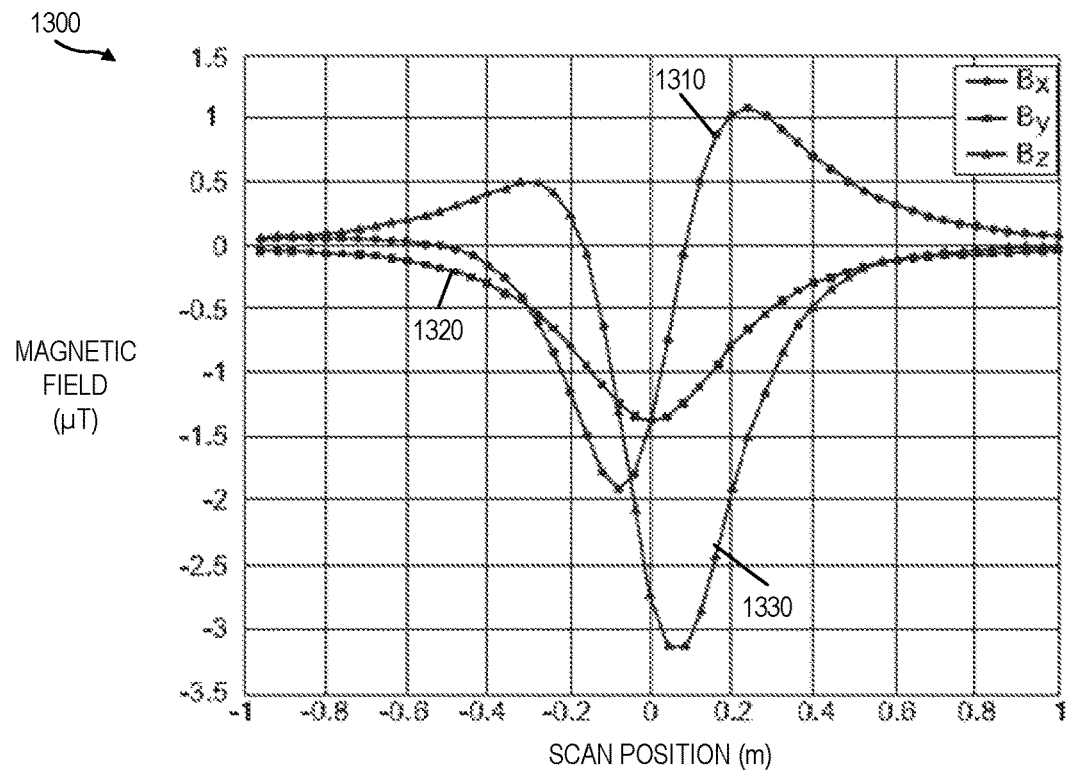
FIG. 13 shows a plot of magnetic field strength versus scan position for a combination dipole model, in an embodiment.

FIG. 13 shows a plot 1300 of exemplary combination magnetic field strength versus scan position, which combines axial, lateral, and vertical dipole orientations of FIGS. 10-12. A dataset 1310 shows magnetic field strength along the x-axis, $B_x$, a dataset 1320 shows magnetic field strength along the y-axis, $B_y$, and a dataset 1330 shows magnetic field strength along the z-axis, $B_z$. $C_x$, $C_y$, and $C_z$ are constants adjusted for model fitting, based on factors including the strength of measured magnetic fields.

Figure 14:
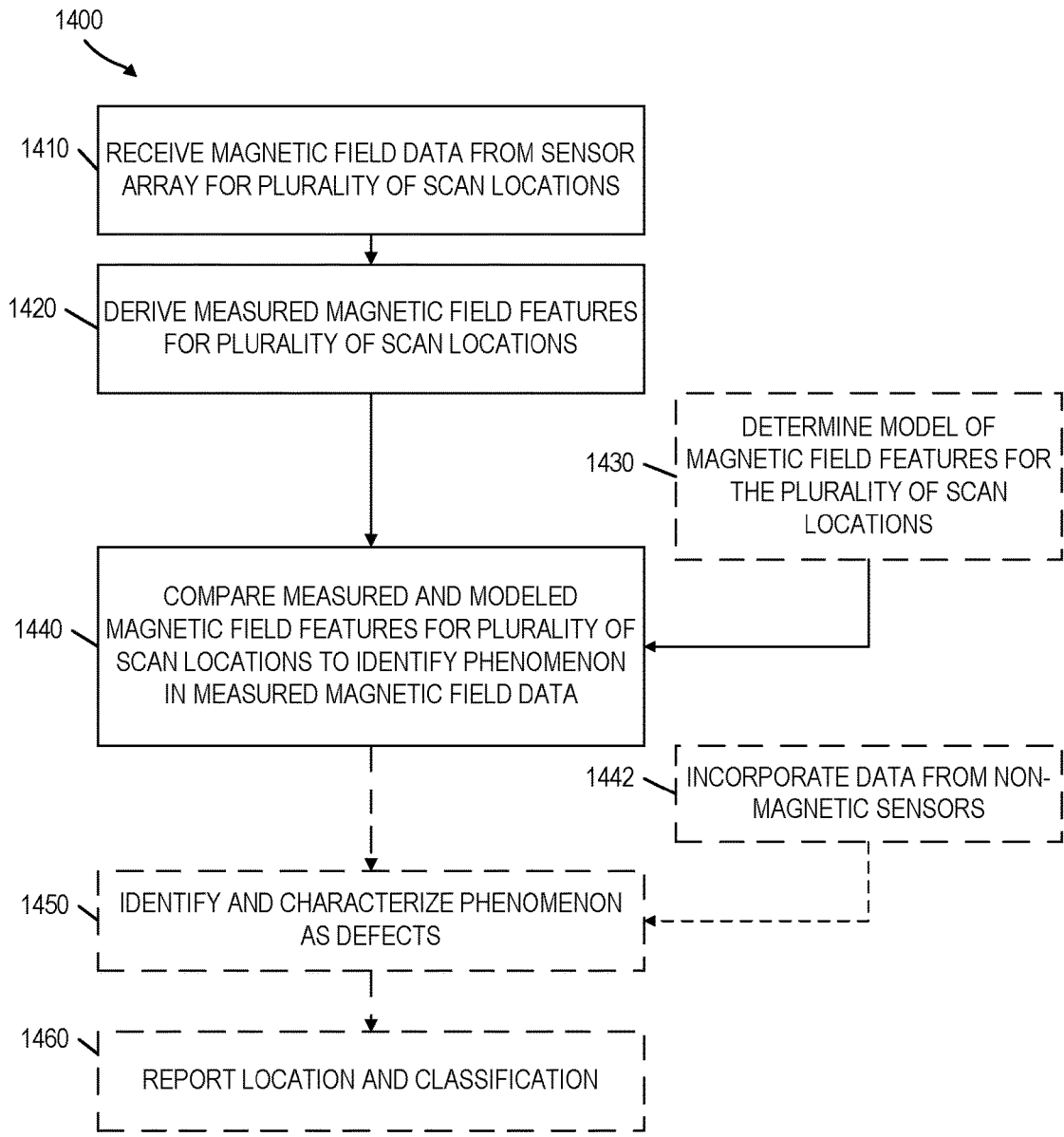
FIG. 14 is a flowchart illustrating steps of a method to characterize a ferromagnetic material, in an embodiment.

Other than comparing models and measurements of magnetic fields over scan position, such as step 650 of method 600, magnetic field gradients may be used to further identify phenomena of ferromagnetic material 130. According to an embodiment, magnetic field gradients are calculated from a plurality of sensors arranged in an array, such as sensor array 300 of FIG. 3. Specifically, FIG. 14 is a flowchart illustrating steps of one method 1400 to detect a phenomenon of a ferromagnetic material and characterize the ferromagnetic material based upon magnetic field data obtained using one or more sensors. Each sensor (e.g. sensors 110, 310, 410) is configured to measure the magnitude and direction of the local magnetic field. Method 1400 uses models and measurements of magnetic fields over scan position to detect and characterize phenomenon 135 of ferromagnetic material 130. Data processing module 150 (or server 160 implementing analysis functions) may perform method 1400 based upon magnetic field data obtained from sensor array 250. Method 1400 may be implemented in data processing module 150 (or server 160) as at least a portion of software 263 and/or firmware 261, FIG. 2. Accordingly, it should be appreciated that method 1400 may also be implemented using system 400, of FIG. 4. Aspects of method 1400 are for example an embodiment of step 650 of method 600.

In step 1410, magnetic field data are received for a plurality of scan positions. In an example of step 1410, processor 264 executes software 263 and/or firmware 261 stored in memory 262 to parse data from sensor array 250, which is received either directly from sensor array 250 or optionally via receiver 255.

In step 1420, magnetic field derived features are derived from the magnetic field data of step 1410. Exemplary magnetic field derived features comprise numerics that are derived from the raw sensor data, or a denoised version thereof, including but not limited to: the field measurements, their Fourier, Wavelet or any other transform, their magnetic field gradients; the gradient Fourier transform, wavelet transform or any other transform; $2^{nd}$ derivative matrices or Hessians, their Fourier transforms or any of their transforms, fractal dimension of the field, gradients, Hessians, or features recovered by data mining or machine learning/deep learning methods.

In an example of step 1420, the magnetic field derived features that are calculated are magnetic field gradients. In such example, the magnetic field gradients are calculated, by data processing module 150 (or server 160), from differences in magnetic fields between sensors 301-310 of sensor array 300, FIG. 3 for a plurality of scan positions. In one embodiment, a single sensor such as sensor 304 measures magnetic fields at a plurality of scan positions, and one or more gradients are calculated, using for example data processing module 150 (or server 160), from the plurality of measurements. In another embodiment, magnetic field gradients between different sensors are calculated for each scan position. Equation 2, below, shows an exemplary calculation for magnetic field gradients between fourth sensor 304 and eighth sensor 308 along the x-axis of FIG. 3.

$$\frac{\Delta B_{xyz}}{\Delta x} = \begin{pmatrix} B_{x_{S4}} - B_{x_{S8}} \\ B_{y_{S4}} - B_{y_{S8}} \\ B_{z_{S4}} - B_{z_{S8}} \end{pmatrix} / x_{S4-S8} \quad (2)$$

In Equation 2, $\Delta B_{xyz}/\Delta x$ is the difference between three-axis magnetic fields between sensor 304 (abbreviated S4) at position $x_{S4}$ and sensor 308 (abbreviated S8) at position $x_{S8}$. $B_{x_{S4}}$ is the x-axis magnetic field at fourth sensor 304, $B_{x_{S8}}$ is the x-axis magnetic field at eighth sensor 308, and so on for y-axis and z-axis magnetic fields, $B_y$, $B_z$. $x_{S4-S8}$ is the spacing distance between sensors 304 and 308.

Three-axis magnetic field gradients are calculated from dipole models of magnetic fields for additional select pairs of sensors in the same manner. For example, three-axis magnetic field gradients ($\Delta B_{xyz}$) are calculated using Equation 3, below, between fourth sensor 304 and ninth sensor 309, between fourth sensor 304 and tenth sensor 310, and between ninth sensor 309 and tenth sensor 310 along the z-axis, as depicted in FIG. 3.

$$\frac{\Delta B_{xyz}}{\Delta z} = \begin{pmatrix} \frac{B_{x_{S4}} - B_{x_{S9}}}{z_{S4-S9}} & \frac{B_{x_{S4}} - B_{x_{S10}}}{z_{S4-S10}} & \frac{B_{x_{S9}} - B_{x_{S10}}}{z_{S9-S10}} \\ \frac{B_{y_{S4}} - B_{y_{S9}}}{z_{S4-S9}} & \frac{B_{y_{S4}} - B_{y_{S10}}}{z_{S4-S10}} & \frac{B_{y_{S9}} - B_{y_{S10}}}{z_{S9-S10}} \\ \frac{B_{z_{S4}} - B_{z_{S9}}}{z_{S4-S9}} & \frac{B_{z_{S4}} - B_{z_{S10}}}{z_{S4-S10}} & \frac{B_{z_{S9}} - B_{z_{S10}}}{z_{S9-S10}} \end{pmatrix} \quad (3)$$

In Equation 3, $\Delta B_{xyz}/\Delta z$ is the difference between three-axis magnetic fields along the z-axis, $z_{S4-S9}$ is the spacing distance between fourth sensor 304 (abbreviated S4) and ninth sensor 309 (abbreviated S9), $B_{x_{S4}}$ is the x-axis magnetic field at fourth sensor 304, $B_{x_{S9}}$ is the x-axis magnetic field at ninth sensor 309, and so on for other sensor pairs and for y-axis and z-axis magnetic fields, $B_y$, $B_z$.

Similarly, select three-axis magnetic field gradients ($\Delta B_{xyz}/\Delta y$) are calculated along the y-axis using Equation 4, below.

$$\frac{\Delta B_{xyz}}{\Delta y} = \begin{pmatrix} \frac{B_{x_{S1}} - B_{x_{S2}}}{y_{S1} - y_{S2}} & \frac{B_{y_{S1}} - B_{y_{S2}}}{y_{S1} - y_{S2}} & \frac{B_{z_{S1}} - B_{z_{S2}}}{y_{S1} - y_{S2}} \\ \frac{B_{x_{S1}} - B_{x_{S3}}}{y_{S1} - y_{S3}} & \frac{B_{y_{S1}} - B_{y_{S3}}}{y_{S1} - y_{S3}} & \frac{B_{z_{S1}} - B_{z_{S3}}}{y_{S1} - y_{S3}} \\ \frac{B_{x_{S1}} - B_{x_{S4}}}{y_{S1} - y_{S4}} & \frac{B_{y_{S1}} - B_{y_{S4}}}{y_{S1} - y_{S4}} & \frac{B_{z_{S1}} - B_{z_{S4}}}{y_{S1} - y_{S4}} \\ \frac{B_{x_{S2}} - B_{x_{S3}}}{y_{S2} - y_{S3}} & \frac{B_{y_{S2}} - B_{y_{S3}}}{y_{S2} - y_{S3}} & \frac{B_{z_{S2}} - B_{z_{S3}}}{y_{S2} - y_{S3}} \\ \frac{B_{x_{S1}} - B_{x_{S5}}}{y_{S1} - y_{S5}} & \frac{B_{y_{S1}} - B_{y_{S5}}}{y_{S1} - y_{S5}} & \frac{B_{z_{S1}} - B_{z_{S5}}}{y_{S1} - y_{S5}} \\ \frac{B_{x_{S2}} - B_{x_{S4}}}{y_{S2} - y_{S4}} & \frac{B_{y_{S2}} - B_{y_{S4}}}{y_{S2} - y_{S4}} & \frac{B_{z_{S2}} - B_{z_{S4}}}{y_{S2} - y_{S4}} \\ \frac{B_{x_{S1}} - B_{x_{S6}}}{y_{S1} - y_{S6}} & \frac{B_{y_{S1}} - B_{y_{S6}}}{y_{S1} - y_{S6}} & \frac{B_{z_{S1}} - B_{z_{S6}}}{y_{S1} - y_{S6}} \\ \frac{B_{x_{S2}} - B_{x_{S5}}}{y_{S2} - y_{S5}} & \frac{B_{y_{S2}} - B_{y_{S5}}}{y_{S2} - y_{S5}} & \frac{B_{z_{S2}} - B_{z_{S5}}}{y_{S2} - y_{S5}} \\ \frac{B_{x_{S3}} - B_{x_{S4}}}{y_{S3} - y_{S4}} & \frac{B_{y_{S3}} - B_{y_{S4}}}{y_{S3} - y_{S4}} & \frac{B_{z_{S3}} - B_{z_{S4}}}{y_{S3} - y_{S4}} \\ \frac{B_{x_{S1}} - B_{x_{S7}}}{y_{S1} - y_{S7}} & \frac{B_{y_{S1}} - B_{y_{S7}}}{y_{S1} - y_{S7}} & \frac{B_{z_{S1}} - B_{z_{S7}}}{y_{S1} - y_{S7}} \\ \frac{B_{x_{S2}} - B_{x_{S6}}}{y_{S2} - y_{S6}} & \frac{B_{y_{S2}} - B_{y_{S6}}}{y_{S2} - y_{S6}} & \frac{B_{z_{S2}} - B_{z_{S6}}}{y_{S2} - y_{S6}} \\ \frac{B_{x_{S3}} - B_{x_{S5}}}{y_{S3} - y_{S5}} & \frac{B_{y_{S3}} - B_{y_{S5}}}{y_{S3} - y_{S5}} & \frac{B_{z_{S3}} - B_{z_{S5}}}{y_{S3} - y_{S5}} \\ \frac{B_{x_{S3}} - B_{x_{S6}}}{y_{S3} - y_{S6}} & \frac{B_{y_{S3}} - B_{y_{S6}}}{y_{S3} - y_{S6}} & \frac{B_{z_{S3}} - B_{z_{S6}}}{y_{S3} - y_{S6}} \\ \frac{B_{x_{S4}} - B_{x_{S5}}}{y_{S4} - y_{S5}} & \frac{B_{y_{S4}} - B_{y_{S5}}}{y_{S4} - y_{S5}} & \frac{B_{z_{S4}} - B_{z_{S5}}}{y_{S4} - y_{S5}} \\ \frac{B_{x_{S2}} - B_{x_{S7}}}{y_{S2} - y_{S7}} & \frac{B_{y_{S2}} - B_{y_{S7}}}{y_{S2} - y_{S7}} & \frac{B_{z_{S2}} - B_{z_{S7}}}{y_{S2} - y_{S7}} \\ \frac{B_{x_{S4}} - B_{x_{S6}}}{y_{S4} - y_{S6}} & \frac{B_{y_{S4}} - B_{y_{S6}}}{y_{S4} - y_{S6}} & \frac{B_{z_{S4}} - B_{z_{S6}}}{y_{S4} - y_{S6}} \\ \frac{B_{x_{S3}} - B_{x_{S7}}}{y_{S3} - y_{S7}} & \frac{B_{y_{S3}} - B_{y_{S7}}}{y_{S3} - y_{S7}} & \frac{B_{z_{S3}} - B_{z_{S7}}}{y_{S3} - y_{S7}} \\ \frac{B_{x_{S5}} - B_{x_{S6}}}{y_{S5} - y_{S6}} & \frac{B_{y_{S5}} - B_{y_{S6}}}{y_{S5} - y_{S6}} & \frac{B_{z_{S5}} - B_{z_{S6}}}{y_{S5} - y_{S6}} \\ \frac{B_{x_{S4}} - B_{x_{S7}}}{y_{S4} - y_{S7}} & \frac{B_{y_{S4}} - B_{y_{S7}}}{y_{S4} - y_{S7}} & \frac{B_{z_{S4}} - B_{z_{S7}}}{y_{S4} - y_{S7}} \\ \frac{B_{x_{S5}} - B_{x_{S7}}}{y_{S5} - y_{S7}} & \frac{B_{y_{S5}} - B_{y_{S7}}}{y_{S5} - y_{S7}} & \frac{B_{z_{S5}} - B_{z_{S7}}}{y_{S5} - y_{S7}} \\ \frac{B_{x_{S6}} - B_{x_{S7}}}{y_{S6} - y_{S7}} & \frac{B_{y_{S6}} - B_{y_{S7}}}{y_{S6} - y_{S7}} & \frac{B_{z_{S6}} - B_{z_{S7}}}{y_{S6} - y_{S7}} \end{pmatrix} \quad (4)$$

In Equation 4, $\Delta B_{xyz}/\Delta y$ is the difference between three-axis magnetic fields along the y-axis, $y_{S1-S2}$ is the spacing distance between first sensor 301 (abbreviated S1) and second sensor 302 (abbreviated S2), $B_{xS1}$ is the x-axis magnetic field at first sensor 301, $B_{xS2}$ is the x-axis magnetic field at second sensor 302, and so on for other sensor pairs and for y-axis and z-axis magnetic fields, $B_y$ and $B_z$.

In an example of step 1420, x-axis magnetic field gradients ($\Delta B_{xyz}/\Delta x$) are calculated using Equation 2 from differences between three-axis magnetic fields ($B_x$, $B_y$, $B_z$) measured with fourth sensor 304 (S4) and eighth sensor 308 (S8) along the x-axis as depicted in FIG. 3. Similarly, select z-axis magnetic field gradients ($\Delta B_{x,y,z}/\Delta z$) are calculated using Equation 3 for magnetic fields measured with fourth sensor 304 (S4), ninth sensor 309 (S9), and tenth sensor 310 (S10), along the z-axis, as depicted in FIG. 3. Similarly, select y-axis magnetic field gradients ($\Delta B_{x,y,z}/\Delta y$) are calculated using Equation 4 for magnetic fields measured with first sensor 301 (S1), second sensor 302 (S2), third sensor 303 (S3), fourth sensor 304 (S4), fifth sensor 305 (S5), sixth sensor 306 (S6), and seventh sensor 307 (S7), along the y-axis, as depicted in FIG. 3. Exemplary measured magnetic field gradients are plotted in FIG. 15.

Figure 15:
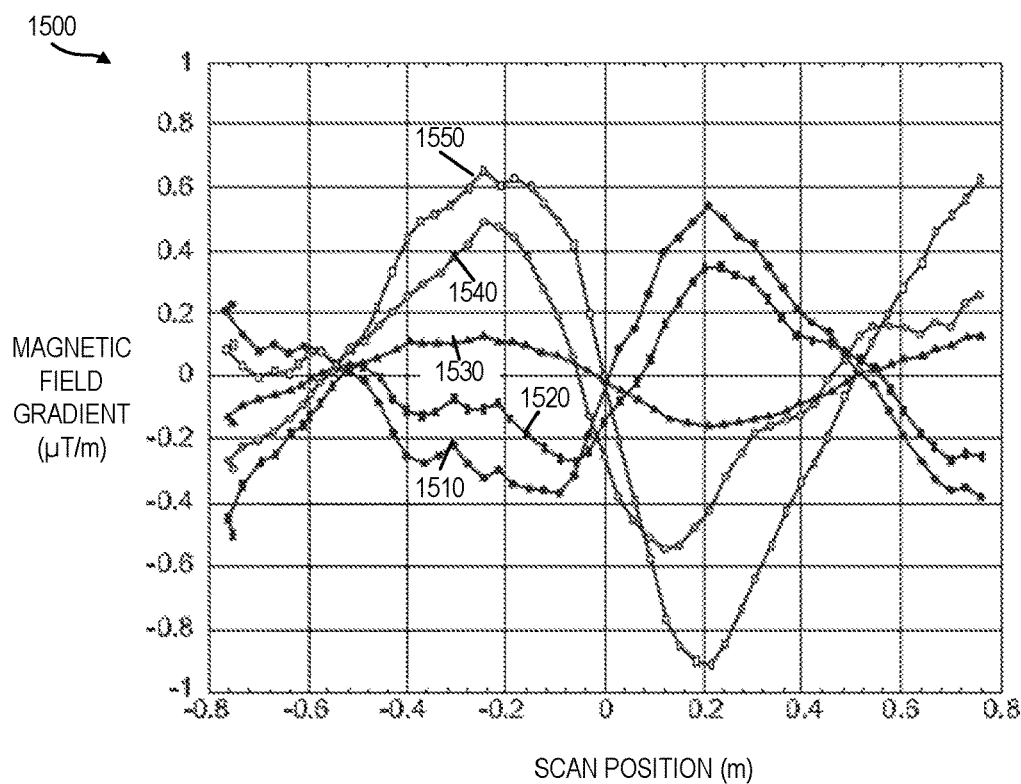
FIG. 15 shows a plot of measured magnetic field gradients versus scan position, in an embodiment.

FIG. 15 shows a plot 1500 of exemplary measured magnetic field gradients in the x-axis versus scan position. Plot 1500 is determined by data processing module 150 from magnetic field 140 of defect 350 measured using sensor array 300 of FIG. 3 for example. Dataset 1510 shows a first gradient $\Delta B_x$ between first sensor 301 and second sensor 302. Dataset 1520 shows a second gradient $\Delta B_x$ between first sensor 301 and third sensor 303. Dataset 1530 shows a third gradient $\Delta B_x$ between first sensor 301 and fourth sensor 304. Dataset 1540 shows a fourth gradient $\Delta B_x$ between third sensor 303 and fourth sensor 304. Dataset 1550 shows a fifth gradient $\Delta B_x$ between third sensor 303 and fifth sensor 305.

Although step 1420 is described above including measured magnetic field gradients, it should be appreciated that other measured magnetic field derived features (other than gradients) could be utilized in step 1420. For example, instead of gradients, step 1420 may calculate measured magnetic field hessians, wavelets, power spectral density, or fractal dimension without departing from the scope hereof. As such, it should be appreciated that, although equations 2-4 above show the formula for gradients, step 1420 may be implemented based on similar formulas for many other magnetic field derived features that are derived from the magnetic field sensor data, such as those magnetic field derived features discussed above.

Figure 16:
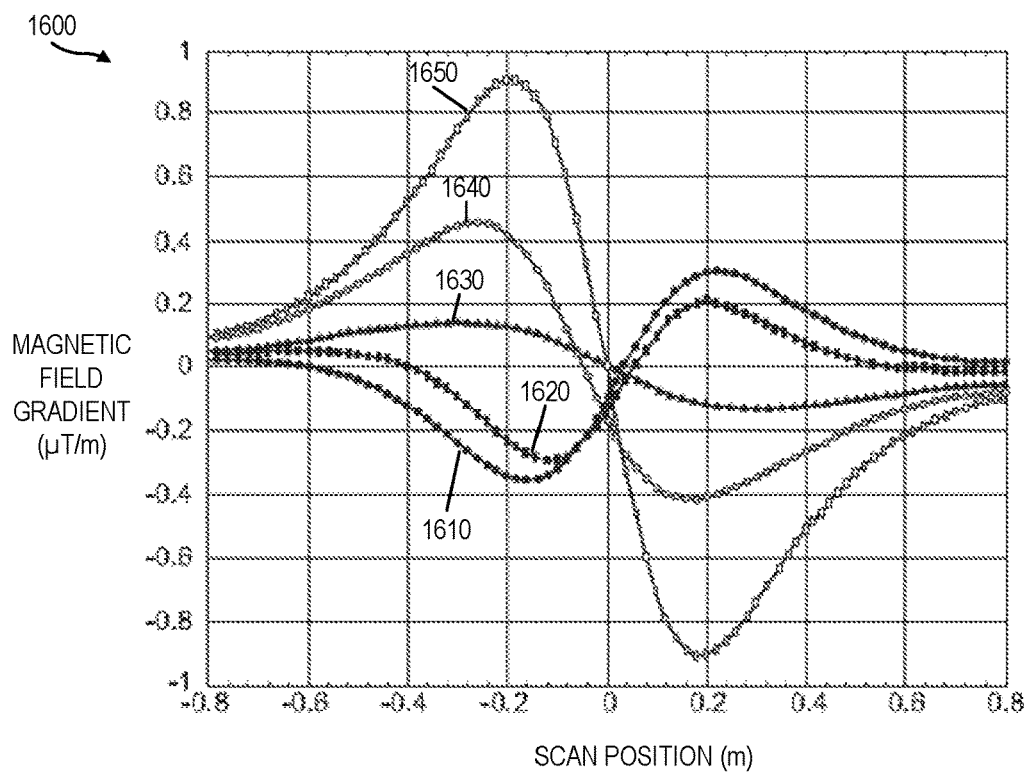
FIG. 16 shows a plot of dipole model magnetic field gradients versus scan position, in an embodiment.

In an embodiment, method 1400 includes optional step 1430, wherein at least one model of magnetic field derived features is calculated from modeled magnetic fields for a plurality of scan positions. In an example of step 1430, modeled magnetic field gradients shown in FIG. 16 are calculated by data processing module 150 (or server 160) using Equations 2-4 from model magnetic fields calculated using Equation 1 for select pairs of sensors and a plurality of scan positions. In an alternative embodiment, modeled magnetic field features are calculated from historical data as found in database 162 for the same location. For example, if the same ferromagnetic material 130 was previously scanned using method 600, the measured magnetic field features are used as a model for comparison with repeat measurements. This approach enables (a) monitoring a small anomaly that may be a defect over time to determine if it is growing in size; growth in size is more likely associated with a developing defect than with a weld or flange.

FIG. 16 shows a plot 1600 of exemplary magnetic field gradients in the x-axis versus scan position calculated by data processing module 150 (or server 160) for a dipole model of a defect, such as defect 350 of FIG. 3. Dataset 1610 shows a first gradient $\Delta B_x$ between first sensor 301 and second sensor 302. Dataset 1620 shows a second gradient $\Delta B_x$ between first sensor 301 and third sensor 303. Dataset 1630 shows a third gradient $\Delta B_x$ between first sensor 301 and fourth sensor 304. Dataset 1640 shows a fourth gradient $\Delta B_x$ between third sensor 303 and fourth sensor 304. Dataset 1650 shows a fifth gradient $\Delta B_x$ between third sensor 303 and fifth sensor 305. Again, it should be appreciated that step 1430 is not limited to magnetic field gradients, but can be implemented based on other magnetic field derived features such as those discussed above.

In step 1440, measured magnetic field derived feature data are compared to modeled magnetic field feature data for a plurality of scan positions to identify one or more phenomena in magnetic field features caused by welds, defects, or anomalies in the ferromagnetic material. In an example of step 1440, multiple measured magnetic field gradients from sensor array 300, such as those shown in FIG. 15, are compared, using data processing module 150 (or server 160), to modeled magnetic field gradients, such as those shown in FIG. 16, to identify a phenomenon in magnetic field gradients caused by defect 350 of ferromagnetic material 330 of FIG. 3. As part of step 1440, measured and modeled data may be analyzed for correct dipole orientation based on dipole model gradients.

According to an embodiment, select magnetic field phenomena containing a defect signature are used to identify defect 350. According to another embodiment, step 1440 includes an optional step 1442 of incorporating data from non-magnetic sensors 252 of FIG. 2 to further enhance characterization of ferromagnetic material 130. In one example, non-magnetic sensors 252 provide ground penetrating radar used to measure standoff distance 312. In another example, data processing module 150 utilizes GPS location information provided by GPS 156 for each magnetic field measurement, which may be augmented by one or both of Wide Area Augmentation System (WAAS) data and odometer data.

In an optional step 1450, one or more defects or irregularities of a ferromagnetic material are characterized, and their locations and classifications may be reported in step 1460. In an example of step 1450, defect 350 of FIG. 3 is identified and characterized. In an example of step 1460, location of defect 350 is reported to server 160 and stored in database 162, FIG. 1. Reporting location of defects and irregularities includes displaying two and three-dimensional plots on interface 265 of data processing module for example. Depending on the type of phenomenon identified, a more intrusive inspection, such as digging out an underground pipe for visual inspection, may be performed in the identified locations.

Characterization of a defect by data processing module 150 in step 1450 may include determining its size and orientation, and may further include classifying a type of missing metal defect. Characterization may include distinguishing between a defect and a non-defect such as a weld, flange, coupled branch line, bend, or other normal or intentional anomaly. Identification and characterization of defects and irregularities may be assisted using information from different sensor types and prior magnetic sensor data for the same location. Method 1400 provides advantages for identifying and characterizing phenomena in ferromagnetic material including that the method may be automated and is repeatable.

Figure 17:
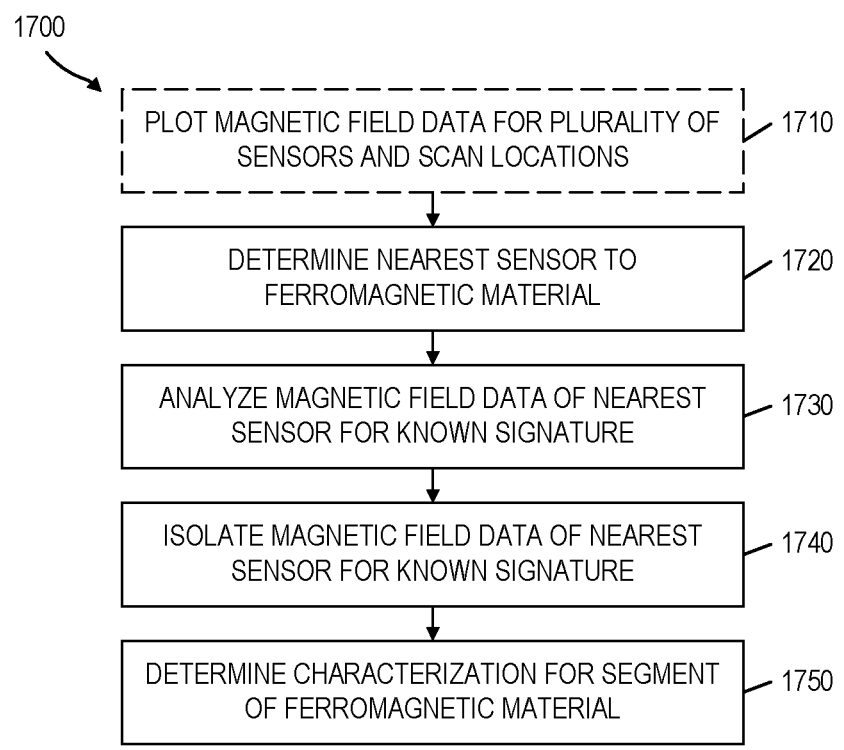
FIG. 17 shows steps for determining magnetic field gradients in FIG. 14, in an embodiment.

FIG. 17 shows an exemplary method 1700 for determining a model, and thus a signature, for observed magnetic field gradients. Method 1700 is an embodiment of aspects of FIG. 14.

In one embodiment, method 1700 includes a step 1710 of plotting magnetic field data for a plurality of locations and a plurality of sensors via interface 265 for analysis by a user to determine a nearest sensor to a magnetic field source. For example, plot 800 of FIG. 8 may be analyzed for a weld signature from measurements made of weld 535 of FIG. 5 using method 600 of FIG. 6. Step 1710 may occur in method 1400 prior to step 1410.

In a step 1720, a nearest sensor of the sensor array to a phenomenon of the ferromagnetic material is determined. In one embodiment, data processing module 150 determines the nearest sensor. In an example of this embodiment of step 1720, processor 264 executes a portion of software 263 and/or firmware 261 to process magnetic field data generated by sensors 301-310 of FIG. 3 to determine that sensor 304 of FIG. 3 is nearest defect 350. In another embodiment, a user identifies sensor 304 as the nearest sensor to defect 350 by visually inspecting magnetic field plots displayed in step 1710. Step 1720 may occur in method 1400 between steps 1410 and 1420.

In a step 1730, magnetic field data from the nearest sensor, measured over a plurality of scan positions, are analyzed for known signatures. In an example of step 1730, using data processing module 150, magnetic field data from nearest sensor 304 of FIG. 3 are analyzed for signatures of one or more known phenomena in ferromagnetic material, such as weld 535 of FIG. 5. In an embodiment of step 1730, measured magnetic fields versus scan position along the ferromagnetic material, such as in plot 800 of FIG. 8, are compared to a magnetic dipole model versus scan position, such as in plot 900 of FIG. 9. In an embodiment of step 1730, known signatures are analyzed via data processing module 150 using matched filters and statistical-detection algorithms.

If a signature is found in step 1730, a step 1740 isolated a portion of the magnetic field data that matches a known signature. In an example of step 1740, using data processing module 150, magnetic field data corresponding to a weld signature from weld 535 of FIG. 5 are isolated from magnetic field data of first and second pipe segments 531, 532. According to an embodiment, a user crops magnetic field data using data processing module 150 to isolate a weld signature. For example, plot 800 of FIG. 8 may be cropped between scan positions to a narrower window ranging from −1.7 m to 1.8 m to isolate the weld signature.

Steps 1730 and 1740 may occur in method 1400 between steps 1440 and 1450. For example, if steps 1730 and 1740 are used in method 1400, step 1730 may act to filter out known non-defects (such as welds) from the phenomenon identified in step 1440. Steps 1730 and 1740 may utilize non-magnetic sensors, such as GPS, and ground penetrating radar, as discussed above with respect to step 1442 to further enhance identification of known non-defects in method 1700.

In a step 1750, a characterization is determined for the segment of ferromagnetic material having a phenomenon. Step 1750 acts to identify the phenomenon as defects, and then potentially characterize said identified phenomenon as a specific type of defect. The characterization and phenomenon location are then reported in step 1460, FIG. 14. In an example of step 1750, using data processing module 150, magnetic flux leakage at weld 535 of pipe 530, FIG. 5 is analyzed to determine a magnetization direction and a magnetization amplitude (or strength) for first and second segments 531, 532.

In an embodiment, using data processing module 150 (or server 160), modeled magnetic data is modeled as a linear subspace of components of the magnetic signal over scan position, such as gradients, wavelets, and power spectral density. The magnetic signal components are extracted from a physics-based model, such as a dipole model, and corrupted with noise and interference from one or more magnetic sources to make the model more realistic. Magnetic sensor measurements are then projected onto the subspace spanned by dipole moments, or any function of the magnetic dipole moments, such as gradients, Hessians, wavelets, power spectral density, or fractal dimension of other magnetic field derived features discussed above. Equation 5a shows an example linear subspace model.

$$X = S\theta + F\varphi + U\psi + n \quad (5a)$$

In Equation 5a, X is a gradient measurement vector across scan positions, S is a feature subspace basis matrix across scan positions in terms of gradients, F is a known magnetic interference subspace such as a bias or flange, U is an unknown magnetic interference subspace matrix, n is a noise vector, and θ, φ, and ψ are scaling parameter vectors determined from measurements. U may be constructed as the matrix orthogonal to a concatenation of S and F.

Again, it should be appreciated that X may represent feature measurement vectors other than gradient. For example, within Equation 5a, the subspace basis matrix S is based on gradients, but it should be appreciated that the subspace basis matrix S may be based on other magnetic field measurements such as those magnetic field derived features discussed above. In an embodiment, subspace basis matrix S is physics dipole moment based. In this embodiment, the phenomena of interest within the measured magnetic field data are made of dipoles (geometric shapes discussed above), with a varying magnitude (small vs. large defects, defects vs. weld, etc.) In another embodiment, the subspace basis matrix S is constructed based on learning techniques such as Singular Value Decomposition (SVD), Espirit, and Music algorithms.

Equation 5a linearly models the phenomenon identified within the magnetic field raw data. Using equation 5a, data processing module 150 (or server 160) can both identify and characterize a detected phenomenon within the measured magnetic field data. For example, within data processing module 150 (or server 160) and using equation 5a, for a given phenomenon, a window size W is selected. Within that window, magnetic field derived features are determined. The window size W may be adjusted for sensitivity to features of different sizes. For example, a small window size W may be used to aim detection at small-scale features, whereas a larger window size W may be used to aim detection at larger-scale features. In another example, the same dataset may be analyzes using two or more different window sizes to be sensitive to features of a variety of sizes. In the above example of gradients, computations of equations 2-4, over the determined window W, derived from all possible pairs of sensor measurements, provide the canonical shape of what a gradient of the magnetic field for any event looks like. Equation 5a's modulation by the vector θ determines whether a dipole moment based phenomenon is present. If the magnitude of θ is above a threshold, then the phenomena contains a defect (or in other words a defect is detected). The direction of the vector θ may be utilized to characterize the phenomena, as discussed below. 4) The matrix F represents other known events that may be non-dipole moment based, or different. F is computed as in equation 3.

It should be appreciated that non-linear models may be utilized instead of the linear model shown in equation 5a. For example, non-linear models would include an equation 5b.

$$X=S(\theta)+F(\varphi)+n \quad (5b)$$

S, F are a non-linear function of θ, φ. Under equation 5b, either S, F, or both, may be learned using non-linear curve fitting, neural networks, deep-learning algorithms, etc. For each phenomenon within the measured magnetic field data, S (or F) may have its own shape.

A hypothesis test may be used to determine whether the measured magnetic field data does not (null hypothesis, H0) or does (first hypothesis, H1) include a phenomenon signature that is a defect. Equations 6 and 7 state an exemplary hypothesis test based on equation 5a, but may be modified as understood by those of ordinary skill based on equation 5b, above.

$$H0: X=F\varphi+N\psi+n \quad (6)$$

Equation 6 shows null hypothesis, H0, which states that the gradient measurement vector across scan positions, X, is due to (a) known interference subspace, F, plus (b) a subspace N which is the subspace orthogonal to the projection of subspace S onto the subspace orthogonal to known interference subspace F, and (c) noise vector n. Herein, each of F, N, and S interchangeably refers to the respective matrix as well as the subspace spanned by the columns of the matrix.

$$H1: X=S\theta+F\varphi+n \quad (7)$$

Equation 7 shows first hypothesis, H1, which states that the gradient measurement vector across scan positions, X, is due to feature subspace basis matrix across scan positions in terms of gradients, S, plus known interference subspace, F, and noise vector n.

Figure 9C:
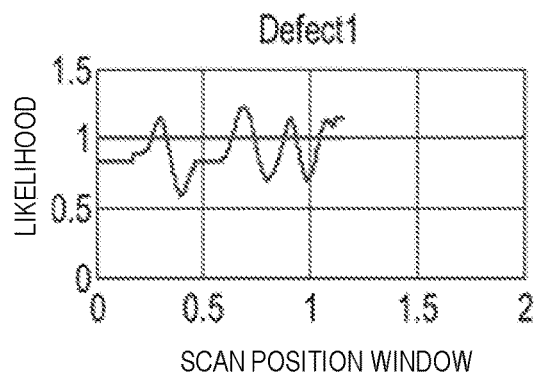
FIG. 9C and FIG. 9D represent plots of magnetic field gradients versus scan position in presence of a defect.
Figure 9D:
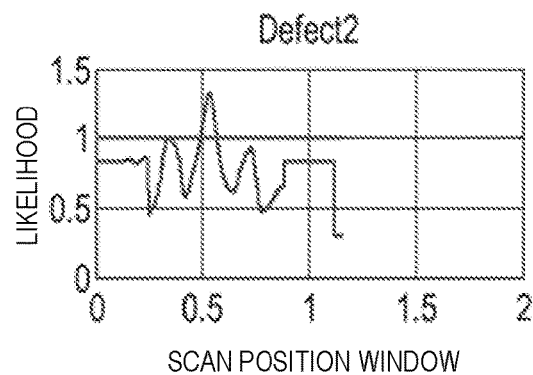

The output of the hypothesis test of Equations 6 and 7 is a statistic proportional to the likelihood, L, of a phenomenon being present. Equations 6 and 7 may be graphically understood with respect to FIGS. 9A-D, where hypothesis H0 is shown in FIGS. 9A and 9B because only welds are shown and the likelihood never crosses threshold. By contrast, FIGS. 9C-D show hypothesis H1 because defects 1 and 2 are shown and the likelihood crosses the threshold.

Thus, it is shown that a defect may be identified in a binary manner (e.g. presence versus absence of defect, but not yet classified to determine the type of defect). The likelihood compares the observed value X of equation 5 to a threshold. This decision may be made by selecting the most likely event, which is the phenomenon in a dictionary of phenomena that most closely resembles the measurement X, preferably (but not necessarily) after accounting for noise in the data. This decision may utilize a hypothesis test, as shown in equations 6 and 7, or alternatively/additionally, a nearest neighbor model, or any other pattern classification/machine learning/deep-learning algorithm. To compensate for noise, statistic used thereby may be a Chi-Square statistic, an F statistic, or non-Gaussian generalization of the Chi-Square or F statistic such as those discussed in: M N Desai, R S Mangoubi, "Robust Gaussian and non-Gaussian matched subspace detection," IEEE Transactions on Signal Processing, 2003.

It should be appreciated that functions other than the likelihood function may be utilized, such as the robust likelihood function which is a trimmed version of the likelihood function that protects against noise outliers. Moreover, the estimate of θ, φ, or $\hat{\theta}$, $\hat{\phi}$, may be obtained by inverting the matrix or functions (non-linear models) S, F, respectively. The magnitude and direction of these vectors may then be used instead of the likelihood function. Embodiments where the noise model is unknown and the non-parametric approach is used, may use non-parametric statistics such as the sign test, the rank sum test, rank histograms of the noise, etc.

The magnitude of phenomenon scaling parameter vector, θ, may be a statistic for determining the presence of a phenomenon, the size of the phenomenon, and the magnetization direction of the phenomenon.

In an embodiment, modeled magnetic data is modeled as a non-linear subspace of components of the magnetic signal versus scan position, such as a polynomial, neural network, or learning-based technique, fitted to a measured magnetic field data curve. The coefficients of the non-linear subspace may include components that determine the presence of phenomena and characterize the nature of those phenomena. In another embodiment, a fractal dimension of the measured magnetic field data is used to determine the presence of phenomena and to characterize the nature of those phenomena.

It should be appreciated that the models of Eq. 5a and 5b may be replaced by models not based on feature subspaces S and F.

Figure 18:
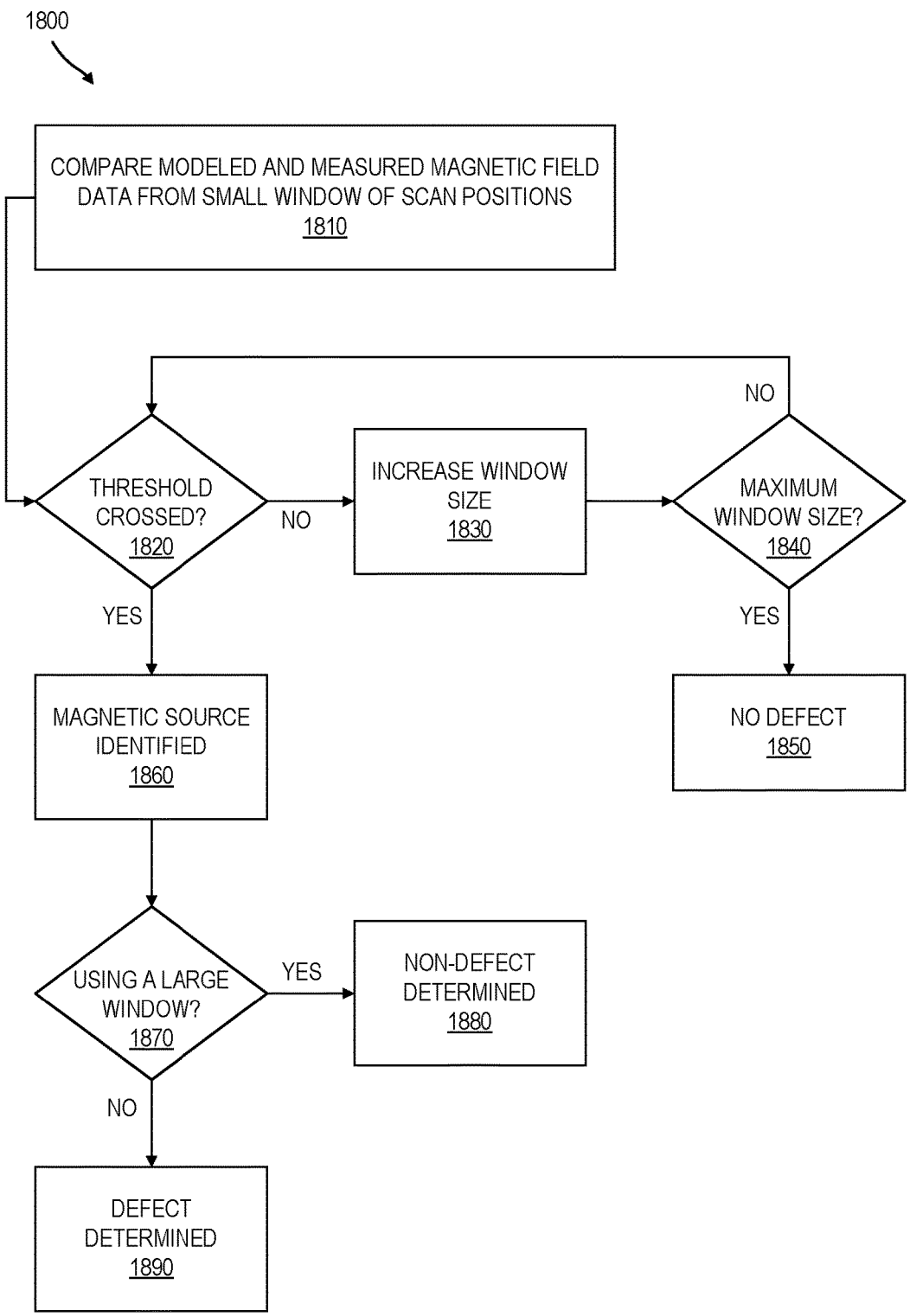
FIG. 18 is a flow chart for a method to identify a phenomenon within ferromagnetic material, in an embodiment.

FIG. 18 is a flowchart for a method 1800 to identify a phenomenon within ferromagnetic material by comparing modeled and magnetic field data over a variable window of scan positions. In step 1810, method 1800 compares modeled and magnetic field data, such as gradient data, from a small window of scan positions corresponding to a portion of a ferromagnetic material. In one example of operation of step 1800, data processing module 150 compares modeled magnetic field data to captured magnetic field data, captured using one or more of sensors 350 of FIG. 3, corresponding to a window of scan positions along ferromagnetic material 130. Method 1800 is an example of steps 1440-1450 and 1750 of FIGS. 14 and 17, respectively.

Step 1820 is a decision. If step 1820 determines that a likelihood, L, has crossed a predefined threshold indicating that a phenomenon is present in the ferromagnetic material, then method 1800 proceeds with step 1860. Otherwise, method 1800 proceeds with step 1830 to increase window size. In an example of step 1820, L has crossed a predefined likelihood threshold of for example one (L>1), as shown in FIGS. 9C and 9D, indicating presence of a defect within a scan position window from zero to one along the x-axis. In another example of step 1820, L has not crossed the predefined threshold of one (L<1) in a scan window from zero to one, as shown in FIGS. 9A and 9B, indicating absence of a defect. The predefined likelihood threshold may take on other values than one, without departing from the scope thereof. For example, the predefined likelihood threshold may depend on whether or not the likelihood L has been normalized and the nature of such normalization. Step 1820 is an example of step 1450 and 1750 of methods 1400 and 1700, respectively.

In optional step 1830, the window size is increased. In an example of step 1830, the window for comparing measured and modeled magnetic field data is increased to the entire range of zero to two shown in FIGS. 9A-9D. Window as used herein means the number of data points surrounding, or beginning from, a given scan position in the measured magnetic field data.

Step 1840 is a decision. If, in step 1840, the window size has been increased to maximum, method 1800 proceeds to step 1850, which determines that no defect is present in the corresponding portion of ferromagnetic material. Otherwise, method 1800 returns step 1820 to determine if the likelihood threshold has been crossed. In an example of step 1840, the window size corresponds to scan positions taken along first segment 531 of pipe 530, FIG. 5, which is not a maximum window and method 1800 returns to step 1820. Steps 1830 to 1860 together form an example of step 1440 of method 1400.

In step 1860, a magnetic field source is identified. In an example of step 1860, a magnetic field phenomenon is identified from defect 450, FIG. 4.

Step 1870 is a decision. If in step 1870, a large window is determined to have been used, then control passes to step 1880 where a non-defect is determined. In an example of step 1830, a window covering scan positions for first and second pipe segments 531, 532 of FIG. 5 was used and the magnetic source identified in step 1860 was from weld 535. Otherwise, if a large window was not used, for example the window includes data from only first pipe segment 531, method 1800 proceeds to step 1890, which determines that a defect is present within the scan positions of the ferromagnetic material corresponding to the window. Steps 1860 and 1870 are examples of step 1450 of FIG. 14.

Method 1800 uses data windows and may apply steps 1820 to 1840 repeatedly to identify phenomena having different sizes. For example, method 1800 may repeat for each, or a portion, of scan positions within the measured magnetic field data received from sensors 110, 310, 410. Method 1800 may be implemented in a parallel or hierarchical manner, using multiple windows without departing from the scope hereof.

Figure 19:
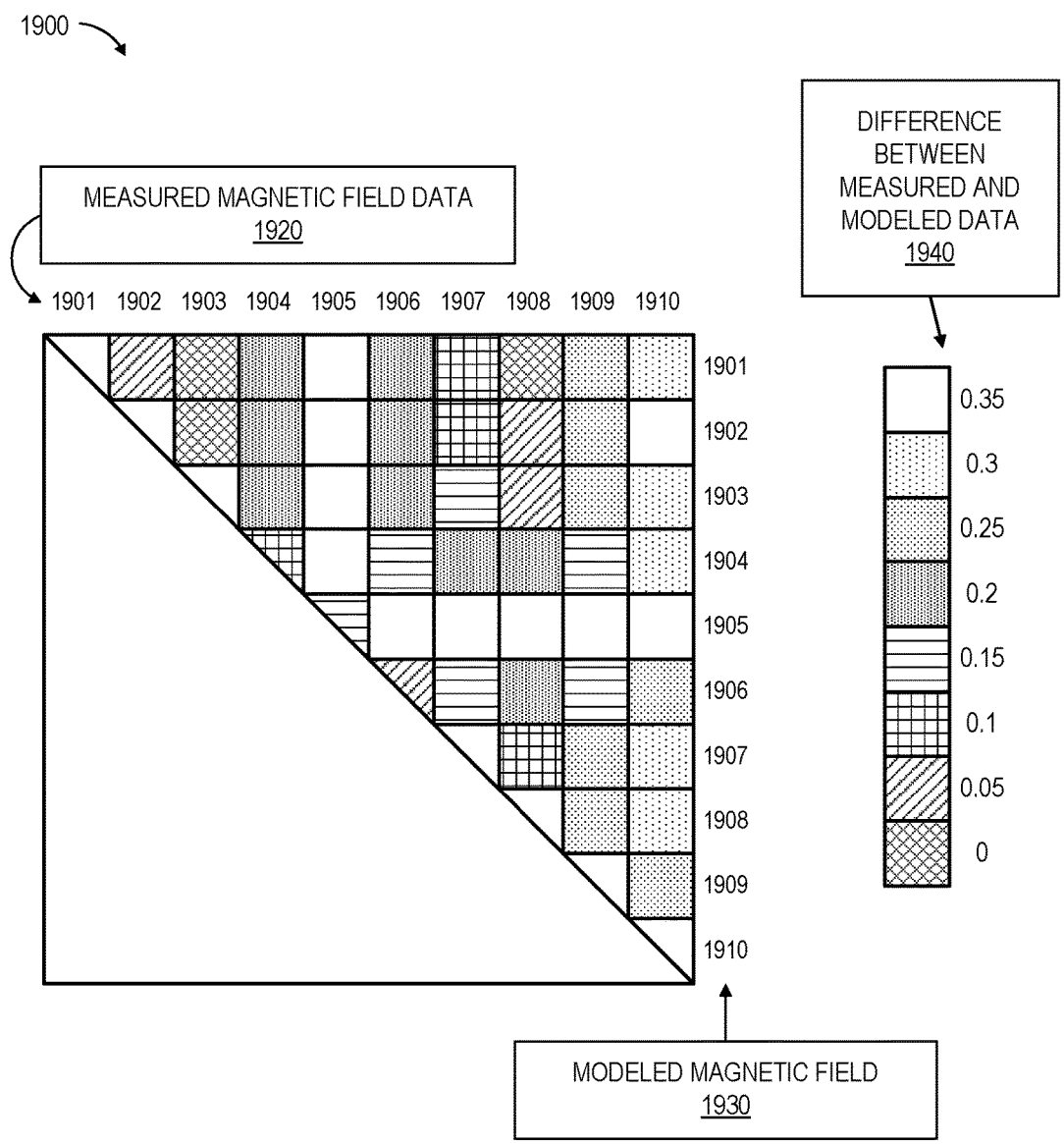
FIG. 19 shows a pairwise statistical comparison plot for characterizing ferromagnetic material, in an embodiment.

FIG. 19 shows a pairwise statistical comparison plot 1900 for characterizing ferromagnetic material. Pairwise statistical comparison plot 1900 may be utilized by methods 1400, 1700, and 1800 to specifically characterize the type of phenomenon, and in some embodiments the type of defect. That is, in addition to determining that a phenomenon occurs within the measured magnetic field data, methods 1400, 1700, and 1800 may utilize plot 1900, or the data therefrom, to determine what the phenomenon is (i.e. type of weld, type of defect, type of anomaly, etc.). Plot 1900 can be stored in server 160 or data processing module 150 and can identify a library of phenomenon that can been seen in the field by systems 100, 200, 400, as well as how different one known phenomenon is to another known phenomenon.

Pairwise statistical comparison plot 1900 is built by comparing the measure of divergence for each pair of phenomena. Specifically, FIG. 19 shows pairwise statistical comparison plot 1900 of features extracted from the measured magnetic field data 1920 (such as the angle between the vector θ for different phenomena) versus modeled magnetic field 1930 for ten different phenomena 1901-1910. In another embodiment, a finite element based model is used in place of modeled magnetic field 1930. The ten phenomena include for example three welds 1901, 1902, 1903, which are examples of weld 535, FIG. 5; phenomenon 1904 which is a small defect; phenomenon 1905 which is a detectable defect, such as defect 450, FIG. 4; and, phenomena 1906-1910 which include other miscellaneous anomalies. Each value in the matrix represents a numerical divergence between pairwise comparisons of measured and modeled magnetic field data for each of the ten phenomena 1901-1910. For example, column 4 "1904", row 1 "1901" represents a pairwise comparison of small defect 1904 to weld 1901. A difference between measured and modeled data is shown with legend 1940. The entries in FIG. 19 are a measure of the statistical divergence between two phenomena, such as a weld and a defect. As such, in FIG. 19, phenomena 1901 and 1908 are separated by a small divergence and are therefore relatively similar, when contrasted to phenomena 1901 and 1905. Alternatively, phenomenon 1901 is more similar to phenomenon 1908, than it is to phenomenon 1905.

The measure of divergence may be based on many variables, and more than one variable may be used to build the pairwise statistical plot of FIG. 19. For example, for two phenomena, we have two estimates of the vector θ, or $\widehat{\theta_1}$, $\widehat{\theta_{1'}}$. The angle between these vectors may be a measure of divergence. The larger the angles, the more distinct are the phenomena (e.g. the larger the divergence), and vice versa. If that angle is not above a threshold, then the phenomena pair is not distinguishable. The threshold may be based on the quality of the measurement, or the sensor noise variance or signal to noise ratio. Other divergences may also be utilized, for example, when non-parametric noise methods are preferred, divergence between histograms or rank histograms may be used. One example is the Kullback Leibler divergence. Divergences derived from machine learning methods are also possible.

To specifically characterize a detected phenomenon using plot 1900, data processing module 150 (or server 160), implementing methods 1400, 1700, or 1800 may utilize a statistic from the test of equations (6) or (7), for instance. Take the case where the matrix F is zero (which could also mean that the matrices S and F are aggregated). The likelihood ratio is compared to a threshold, determining that a phenomenon of interest is present, as discussed above. In turn, data processing module 150 may obtain the estimate of vector $\hat{\theta}$, and compare it to the value vector $\overline{\theta_{1_e}}$, where e can be any of the events 1901 thru 1910. The comparison is based on the angle between vector $\hat{\theta}$ and the given vector $\overline{\theta_{1_e}}$. The comparison yielding the smallest angle indicates the observed phenomenon.

Pairwise statistical plot 1900 may include a machine learning feature where, if the smallest angle between θ, and θ_e, for all events e is above a certain threshold, then the answer would be "event or phenomenon not seen before".

It should be appreciated that the plot 1900 may be just one of many plots analyzed by data processing module 150 (or server 160). For example, there may be multiple plots for each given window size. In such a case, data processing module 150 may obtain multiple divergences for the same pair and fuse at the higher decision level using decision fusion methods, which may be learned using machine learning. Moreover, the system could fuse at the divergence level, and obtain a single fused diversion method, prior to decision.

Figure 20A:
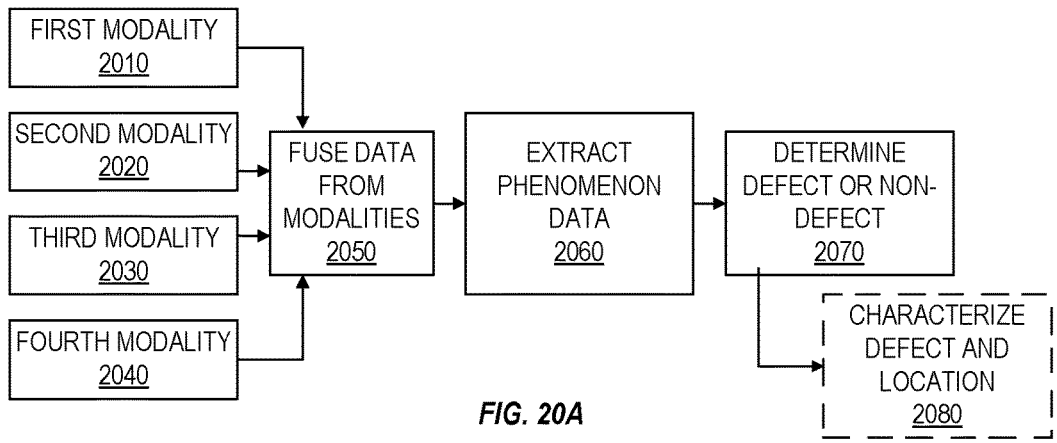
FIG. 20A, FIG. 20B, and FIG. 20C show diagrams of schemes for combining magnetic field data with data from other sensing modalities, in an embodiment.
Figure 20B:
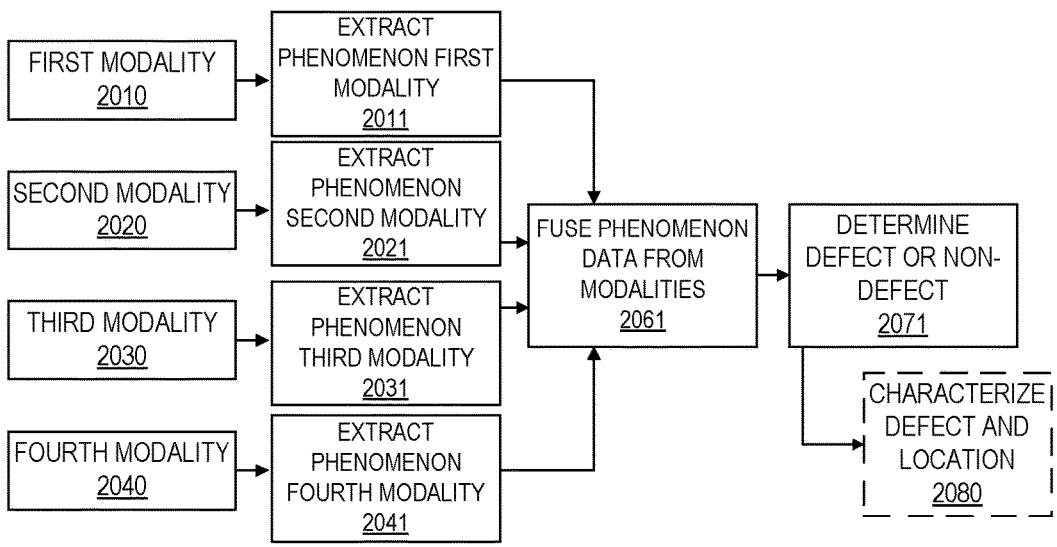
Figure 20C:
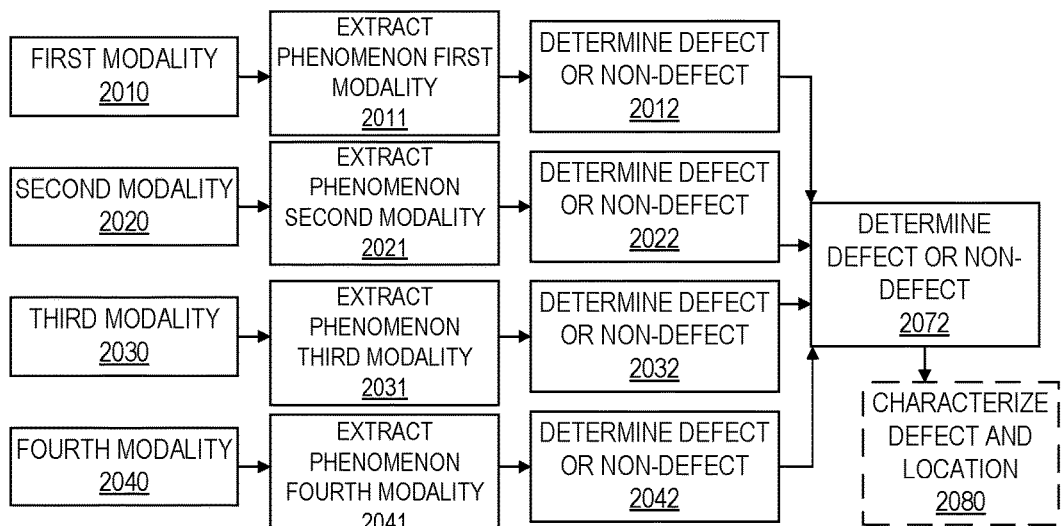

FIGS. 20A, 20B, and 20C show three diagrams of exemplary schemes for combining magnetic field data with data from other sensing modalities, such as ground penetrating radar, multimodal cameras, tomographic measurements, ultrasonic measurements, and active modulated magnetic signals for signal-to-noise ratio enhancement. FIGS. 20A-C are for example diagrams of schemes implementing step 1442 of FIG. 14. Any details extracted from different measurements may be fused, at different levels, such as a measurement level, a data extraction level, or a determination of defect versus non-defect level. FIG. 20A shows a diagram for fusing data from first, second, third and fourth modalities 2010, 2020, 2030, 2040 at a measurement level in step 2050, followed by extracting phenomenon data in step 2060, determining defect versus non-defect in step 2070, and optionally characterizing a defect and its location in step 2080.

FIG. 20B shows a diagram for fusing data at a phenomenon level. Specifically, phenomenon data are extracted for each of the four modalities in steps 2011, 2021, 2031, 2041 and fused in step 2061, followed by determining defect versus non-defect in step 2071 and optionally characterizing a defect and its location in step 2080.

FIG. 20C shows a diagram for fusing data at a defect determining level. Specifically, a defect versus non-defect is determined in steps 2012, 2022, 2032, 2042 from the four modalities 2010, 2020, 2030, 2040 and the determinations are fused in step 2072 to determine defect versus non-defect, and optionally characterizing a defect and its location in step 2080.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which might be said to fall there between.

What is claimed is:

1. A method for characterizing a ferromagnetic material, comprising:
providing a plurality of magnetometers arranged in an at least one-dimensional array, the array being positionable at a standoff distance along a z axis from the ferromagnetic material and translatable along an x axis, perpendicular to the z axis, to a plurality of scan positions along the ferromagnetic material, wherein at least three magnetometers of the plurality of magnetometers are mutually spaced apart and disposed within the array along a first axis;
storing, in a memory, data representing a deterministic physics-based model of magnetic fields for missing metal;
for each scan position of the plurality of scan positions, calculating, by a processor, respective differences between a plurality of respective select pairs of the magnetometers, wherein at least one select pair of the plurality of respective select pairs of the magnetometers comprises two non-adjacent magnetometers of the at least three magnetometers disposed along the first axis, and each select pair of at least two other select pairs of the plurality of respective select pairs of the magnetometers comprises two adjacent magnetometers of the at least three magnetometers disposed along the first axis, and wherein each difference of the respective differences is calculated by dividing by a distance separating the respective select pair of magnetometers; and
comparing, by the processor, respective differences between the plurality of respective select pairs of the magnetometers with the data representing the deterministic physics-based model of magnetic fields for missing metal to identify metal missing from the ferromagnetic material.

2. The method of claim 1, the differences comprising at least one numeric that is derived from magnetic field data measured by at least one magnetometer of the plurality of magnetometers, the numeric being chosen from the group of numerics consisting of: Fourier, Wavelet, magnetic field gradients, gradient Fourier transform, wavelet transform, $2^{nd}$ derivative matrices, Hessians and fractal dimension.

3. The method of claim 1, further comprising characterizing, by the processor, the metal missing from the ferromagnetic material to distinguish between a defect and a non-defect.

4. The method of claim 3, the step of characterizing including applying, by the processor, a pairwise comparison between measured magnetic field data and modeled magnetic field data to characterize the metal missing from the ferromagnetic material.

5. The method of claim 4, the step of applying utilizing a pairwise statistical comparison plot.

6. The method of claim 5, wherein the pairwise statistical plot comprises a plurality of differences between measured magnetic field data and modeled magnetic field data, each difference of the plurality of differences representing a range of values according to a legend.

7. The method of claim 3, the step of characterizing including determining a signature from measured magnetic field data associated with a non-defect of the ferromagnetic material.

8. The method of claim 1, wherein the first axis is the y axis.

9. The method of claim 1, wherein the first axis is the z axis.

10. The method of claim 1, wherein the deterministic physics-based model of magnetic fields for missing metal comprises a magnetic dipole model.

11. The method of claim 10, wherein the magnetic dipole model is calculated according to the equation:

$$\begin{pmatrix} B_x \\ B_y \\ B_z \end{pmatrix} = \frac{1}{r^5} \begin{pmatrix} C_x(3x^2 - r^2) + 3C_y xy + 3C_z xz \\ 3C_x xy + C_y(3y^2 - r^2) + 3C_z yz \\ 3C_x xz + 3C_y yz + C_z(3z^2 - r^2) \end{pmatrix}.$$

12. The method of claim 1, wherein the processor calculates the respective differences between the plurality of respective select pairs of the magnetometers according to the equation:

$$\frac{\Delta B_{xyz}}{\Delta y} = \begin{pmatrix} \frac{B_{x_{S1}} - B_{x_{S2}}}{z_{S1-S2}} & \frac{B_{x_{S1}} - B_{x_{S3}}}{z_{S1-S3}} & \frac{B_{x_{S2}} - B_{x_{S3}}}{z_{S2-S3}} \\ \frac{B_{y_{S1}} - B_{y_{S2}}}{Z_{S1-S2}} & \frac{B_{y_{S1}} - B_{y_{S3}}}{z_{S1-S3}} & \frac{B_{y_{S2}} - B_{y_{S3}}}{z_{S2-S3}} \\ \frac{B_{z_{S1}} - B_{z_{S2}}}{z_{S1-S2}} & \frac{B_{z_{S1}} - B_{z_{S3}}}{z_{S1-S3}} & \frac{B_{z_{S2}} - B_{z_{S3}}}{z_{S1-S3}} \end{pmatrix}$$

where S1, S2 and S3 represent three magnetometers of the at least three magnetometers disposed along the first axis, $\Delta y$ represents distance along the first axis and $B_x$ represents strength of an x-axis magnetic field, $B_y$ represents strength of a y-axis magnetic field and $B_z$ represents strength of a z-axis magnetic field as measured by a respective one of the magnetometers S1, S2 and S3.

13. The method of claim 1, wherein:
the plurality of magnetometers is arranged in an at least two-dimensional array, wherein at least two magnetometers of the plurality of magnetometers are mutually spaced apart and disposed within the array along the x axis; and further comprising:
for each scan position of the plurality of scan positions, calculating, by the processor, respective differences between a plurality of respective select pairs of the magnetometers along the x axis.

14. The method of claim 13, wherein the processor calculates the respective differences between the plurality of respective select pairs of the magnetometers according to the equations:

$$\frac{\Delta B_{xyz}}{\Delta y} = \begin{pmatrix} \frac{B_{x_{S1}} - B_{x_{S2}}}{z_{S1-S2}} & \frac{B_{x_{S1}} - B_{x_{S3}}}{z_{S1-S3}} & \frac{B_{x_{S2}} - B_{x_{S3}}}{z_{S2-S3}} \\ \frac{B_{y_{S1}} - B_{y_{S2}}}{Z_{S1-S2}} & \frac{B_{y_{S1}} - B_{y_{S3}}}{z_{S1-S3}} & \frac{B_{y_{S2}} - B_{y_{S3}}}{z_{S2-S3}} \\ \frac{B_{z_{S1}} - B_{z_{S2}}}{z_{S1-S2}} & \frac{B_{z_{S1}} - B_{z_{S3}}}{z_{S1-S3}} & \frac{B_{z_{S2}} - B_{z_{S3}}}{z_{S1-S3}} \end{pmatrix}$$

and $$\frac{\Delta B_{xyz}}{\Delta x} = \begin{pmatrix} B_{x_{S2}} - B_{x_{S4}} \\ B_{y_{S2}} - B_{y_{S4}} \\ B_{z_{S2}} - B_{z_{S4}} \end{pmatrix} \Big/ x_{S2-S4}$$

where S1, S2 and S3 represent three magnetometers of the at least three magnetometers disposed along the first axis and S2 and S4 represent two magnetometers of the at least two magnetometers disposed along the x axis, $\Delta y$ represents distance along the first axis, $\Delta x$ represents distance along the x axis and $B_x$ represents strength of an x-axis magnetic field, $B_y$ represents strength of a y-axis magnetic field and $B_z$ represents strength of a z-axis magnetic field as measured by a respective one of the magnetometers S1, S2, S3 and S4.

15. The method of claim 1, wherein:
the plurality of magnetometers is arranged in an at least two-dimensional array, wherein at least three magnetometers of the plurality of magnetometers are mutually spaced apart and disposed within the array along a second axis, perpendicular to the first and x axes; and further comprising:
for each scan position of the plurality of scan positions, calculating, by the processor, respective differences between a plurality of respective select pairs of the magnetometers along the second axis, wherein at least one select pair of the plurality of respective select pairs of the magnetometers along the second axis comprises two non-adjacent magnetometers of the at least three magnetometers disposed along the second axis, and each select pair of at least two other select pairs of the plurality of respective select pairs of the magnetometers along the second axis comprises two adjacent magnetometers of the at least three magnetometers disposed along the second axis.

16. The method of claim 15, wherein the processor calculates the respective differences between the plurality of respective select pairs of the magnetometers according to the equations:

$$\frac{\Delta B_{xyz}}{\Delta y} = \begin{pmatrix} \frac{B_{x_{S1}} - B_{x_{S2}}}{z_{S1-S2}} & \frac{B_{x_{S1}} - B_{x_{S3}}}{z_{S1-S3}} & \frac{B_{x_{S2}} - B_{x_{S3}}}{z_{S2-S3}} \\ \frac{B_{y_{S1}} - B_{y_{S2}}}{Z_{S1-S2}} & \frac{B_{y_{S1}} - B_{y_{S3}}}{z_{S1-S3}} & \frac{B_{y_{S2}} - B_{y_{S3}}}{z_{S2-S3}} \\ \frac{B_{z_{S1}} - B_{z_{S2}}}{z_{S1-S2}} & \frac{B_{z_{S1}} - B_{z_{S3}}}{z_{S1-S3}} & \frac{B_{z_{S2}} - B_{z_{S3}}}{z_{S1-S3}} \end{pmatrix}$$

and $$\frac{\Delta B_{xyz}}{\Delta z} = \begin{pmatrix} \frac{B_{x_{S2}} - B_{x_{S5}}}{z_{S2-S5}} & \frac{B_{x_{S2}} - B_{x_{S6}}}{z_{S2-S6}} & \frac{B_{x_{S5}} - B_{x_{S6}}}{z_{S5-S6}} \\ \frac{B_{y_{S2}} - B_{y_{S5}}}{Z_{S1-S5}} & \frac{B_{y_{S2}} - B_{y_{S6}}}{z_{S2-S6}} & \frac{B_{y_{S5}} - B_{y_{S6}}}{z_{S5-S6}} \\ \frac{B_{z_{S2}} - B_{z_{S5}}}{z_{S2-S5}} & \frac{B_{z_{S2}} - B_{z_{S6}}}{z_{S2-S6}} & \frac{B_{z_{S5}} - B_{z_{S6}}}{z_{S5-S6}} \end{pmatrix}$$

where S1, S2 and S3 represent three magnetometers of the at least three magnetometers disposed along the first axis, S2, S5 and S6 represent three magnetometers of the at least three magnetometers disposed along the second axis, $\Delta y$ represents distance along the first axis and $\Delta z$ represents distance along the second axis and $B_x$ represents strength of an x-axis magnetic field, $B_y$ represents strength of a y-axis magnetic field and $B_z$ represents strength of a z-axis magnetic field as measured by a respective one of the magnetometers S1, S2, S3, S5 and S6.

17. The method of claim 16, wherein:
the plurality of magnetometers is arranged in a three-dimensional array, wherein at least two magnetometers of the plurality of magnetometers are mutually spaced apart and disposed within the array along the x axis; and further comprising:
for each scan position of the plurality of scan positions, calculating, by the processor, respective differences between a plurality of respective select pairs of the magnetometers along the x axis.

18. The method of claim 17, wherein the data processor calculates the respective differences between the plurality of respective select pairs of the magnetometers according to the equations:

$$\frac{\Delta B_{xyz}}{\Delta y} = \begin{pmatrix} \frac{B_{x_{S1}} - B_{x_{S2}}}{z_{S1-S2}} & \frac{B_{x_{S1}} - B_{x_{S3}}}{z_{S1-S3}} & \frac{B_{x_{S2}} - B_{x_{S3}}}{z_{S2-S3}} \\ \frac{B_{y_{S1}} - B_{y_{S2}}}{Z_{S1-S2}} & \frac{B_{y_{S1}} - B_{y_{S3}}}{z_{S1-S3}} & \frac{B_{y_{S2}} - B_{y_{S3}}}{z_{S2-S3}} \\ \frac{B_{z_{S1}} - B_{z_{S2}}}{z_{S1-S2}} & \frac{B_{z_{S1}} - B_{z_{S3}}}{z_{S1-S3}} & \frac{B_{z_{S2}} - B_{z_{S3}}}{z_{S1-S3}} \end{pmatrix}$$

and $$\frac{\Delta B_{xyz}}{\Delta z} = \begin{pmatrix} \frac{B_{x_{S2}} - B_{x_{S5}}}{z_{S2-S5}} & \frac{B_{x_{S2}} - B_{x_{S6}}}{z_{S2-S6}} & \frac{B_{x_{S5}} - B_{x_{S6}}}{z_{S5-S6}} \\ \frac{B_{y_{S2}} - B_{y_{S5}}}{Z_{S1-S5}} & \frac{B_{y_{S2}} - B_{y_{S6}}}{z_{S2-S6}} & \frac{B_{y_{S5}} - B_{y_{S6}}}{z_{S5-S6}} \\ \frac{B_{z_{S2}} - B_{z_{S5}}}{z_{S2-S5}} & \frac{B_{z_{S2}} - B_{z_{S6}}}{z_{S2-S6}} & \frac{B_{z_{S5}} - B_{z_{S6}}}{z_{S5-S6}} \end{pmatrix}$$

and $$\frac{\Delta B_{xyz}}{\Delta x} = \begin{pmatrix} B_{x_{S2}} - B_{x_{S4}} \\ B_{y_{S2}} - B_{y_{S4}} \\ B_{z_{S2}} - B_{z_{S4}} \end{pmatrix} \Big/ x_{S2-S4}$$

where S1, S2 and S3 represent three magnetometers of the at least three magnetometers disposed along the y axis, S2, S5 and S6 represent three magnetometers of the at least three magnetometers disposed along the z axis, S2 and S4 represent two magnetometers of the at least two magnetometers disposed along the x axis, $\Delta y$ represents distance along the first axis, $\Delta z$ represents distance along the second axis and $\Delta x$ represents distance along the x axis and $B_x$ represents strength of an x-axis magnetic field, $B_y$ represents strength of a y-axis magnetic field and $B_z$ represents strength of a z-axis magnetic field as measured by a respective one of the magnetometers S1, S2, S3, S4, S5 and S6.

19. The method of claim 1, wherein the data processor compares the respective differences between the plurality of respective select pairs of the magnetometers with the data representing the deterministic physics-based model of magnetic fields for missing metal using a sliding window.

20. A system for characterizing a ferromagnetic material, comprising:
a plurality of magnetometers arranged in an at least one-dimensional array, the array being positionable at a standoff distance along a z axis from the ferromagnetic material and translatable along an x axis, perpendicular to the z axis, to a plurality of scan positions along the ferromagnetic material, wherein at least three magnetometers of the plurality of magnetometers are mutually spaced apart and disposed within the array along a first axis;
a memory storing data representing a deterministic physics-based model of magnetic fields for missing metal; and
a data processor coupled with the plurality of magnetometers and configured to calculate, for each scan position of the plurality of scan positions, respective differences between a plurality of respective select pairs of the magnetometers, wherein at least one select pair of the plurality of respective select pairs of the magnetometers comprises two non-adjacent magnetometers of the at least three magnetometers disposed along the first axis, and each select pair of at least two other select pairs of the plurality of respective select pairs of the magnetometers comprises two adjacent magnetometers of the at least three magnetometers disposed along the first axis, and wherein each difference of the respective differences is calculated by dividing by a distance separating the respective select pair of magnetometers;
wherein the data processor is configured to compare the respective differences between the plurality of respective select pairs of the magnetometers with the data representing the deterministic physics-based model of magnetic fields for missing metal to identify metal missing from the ferromagnetic material.

21. The system of claim 20, wherein distances separating the respective select pairs of magnetometers are adjustable.

22. The system of claim 20, wherein the data processor is configured to calculate a likelihood the metal missing from the ferromagnetic material is a defect and compare the likelihood to a threshold, the metal missing from the ferromagnetic material being a known non-defect if the likelihood is below the threshold, the metal missing from the ferromagnetic material being a defect if the likelihood is above the threshold.

23. The system of claim 20, wherein the memory further stores a pairwise statistical plot, and the data processor is further configured to characterize the metal missing from the ferromagnetic material based on the pairwise statistical plot.

24. The system of claim 23, wherein the pairwise statistical plot comprises a plurality of differences between measured magnetic field data and modeled magnetic field data, each difference of the plurality of differences representing a range of values according to a legend.

25. The system of claim 20, wherein the first axis is the y axis.

26. The system of claim 20, wherein the first axis is the z axis.

27. The system of claim 20, wherein the deterministic physics-based model of magnetic fields for missing metal comprises a magnetic dipole model.

28. The system of claim 27, wherein the magnetic dipole model is calculated according to the equation:

$$\begin{pmatrix} B_x \\ B_y \\ B_z \end{pmatrix} = \frac{1}{r^5} \begin{pmatrix} C_x(3x^2 - r^2) + 3C_y xy + 3C_z xz \\ 3C_x xy + C_y(3y^2 - r^2) + 3C_z yz \\ 3C_x xz + 3C_y yz + C_z(3z^2 - r^2) \end{pmatrix}.$$

29. The system of claim 20, wherein the data processor is configured to calculate the respective differences between the plurality of respective select pairs of the magnetometers according to the equation:

$$\frac{\Delta B_{xyz}}{\Delta y} = \begin{pmatrix} \frac{B_{x_{S1}} - B_{x_{S2}}}{z_{S1-S2}} & \frac{B_{x_{S1}} - B_{x_{S3}}}{z_{S1-S3}} & \frac{B_{x_{S2}} - B_{x_{S3}}}{z_{S2-S3}} \\ \frac{B_{y_{S1}} - B_{y_{S2}}}{z_{S1-S2}} & \frac{B_{y_{S1}} - B_{y_{S3}}}{z_{S1-S3}} & \frac{B_{y_{S2}} - B_{y_{S3}}}{z_{S2-S3}} \\ \frac{B_{z_{S1}} - B_{z_{S2}}}{z_{S1-S2}} & \frac{B_{z_{S1}} - B_{z_{S3}}}{z_{S1-S3}} & \frac{B_{z_{S2}} - B_{z_{S3}}}{z_{S1-S3}} \end{pmatrix}$$

where S1, S2 and S3 represent three magnetometers of the at least three magnetometers disposed along the first axis, $\Delta y$ represents distance along the first axis and $B_x$ represents strength of an x-axis magnetic field, $B_y$ represents strength of a y-axis magnetic field and $B_z$ represents strength of a z-axis magnetic field as measured by a respective one of the magnetometers S1, S2 and S3.

30. The system of claim 20, wherein:
the plurality of magnetometers is arranged in an at least two-dimensional array, wherein at least two magnetometers of the plurality of magnetometers are mutually spaced apart and disposed within the array along the x axis; and
the data processor is further configured to calculate, for each scan position of the plurality of scan positions, respective differences between a plurality of respective select pairs of the magnetometers along the x axis.

31. The system of claim 30, wherein the data processor is configured to calculate the respective differences between the plurality of respective select pairs of the magnetometers according to the equations:

$$\frac{\Delta B_{xyz}}{\Delta y} = \begin{pmatrix} \frac{B_{x_{S1}} - B_{x_{S2}}}{z_{S1-S2}} & \frac{B_{x_{S1}} - B_{x_{S3}}}{z_{S1-S3}} & \frac{B_{x_{S2}} - B_{x_{S3}}}{z_{S2-S3}} \\ \frac{B_{y_{S1}} - B_{y_{S2}}}{z_{S1-S2}} & \frac{B_{y_{S1}} - B_{y_{S3}}}{z_{S1-S3}} & \frac{B_{y_{S2}} - B_{y_{S3}}}{z_{S2-S3}} \\ \frac{B_{z_{S1}} - B_{z_{S2}}}{z_{S1-S2}} & \frac{B_{z_{S1}} - B_{z_{S3}}}{z_{S1-S3}} & \frac{B_{z_{S2}} - B_{z_{S3}}}{z_{S1-S3}} \end{pmatrix}$$

and $$\frac{\Delta B_{xyz}}{\Delta x} = \begin{pmatrix} B_{x_{S2}} - B_{x_{S4}} \\ B_{y_{S2}} - B_{y_{S4}} \\ B_{z_{S2}} - B_{z_{S4}} \end{pmatrix} / x_{S2-S4}$$

where S1, S2 and S3 represent three magnetometers of the at least three magnetometers disposed along the first axis and S2 and S4 represent two magnetometers of the at least two magnetometers disposed along the x axis, $\Delta y$ represents distance along the first axis, $\Delta x$ represents distance along the x axis and $B_x$ represents strength of an x-axis magnetic field, $B_y$ represents strength of a y-axis magnetic field and $B_z$ represents strength of a z-axis magnetic field as measured by a respective one of the magnetometers S1, S2, S3 and S4.

32. The system of claim 20, wherein:
the plurality of magnetometers is arranged in an at least two-dimensional array, wherein at least three magnetometers of the plurality of magnetometers are mutually spaced apart and disposed within the array along a second axis, perpendicular to the first and x axes; and
the data processor is further configured to calculate, for each scan position of the plurality of scan positions, respective differences between a plurality of respective select pairs of the magnetometers along the second axis, wherein at least one select pair of the plurality of respective select pairs of the magnetometers along the second axis comprises two non-adjacent magnetometers of the at least three magnetometers disposed along the second axis, and each select pair of at least two other select pairs of the plurality of respective select pairs of the magnetometers along the second axis comprises two adjacent magnetometers of the at least three magnetometers disposed along the second axis.

33. The system of claim 32, wherein the data processor is configured to calculate the respective differences between the plurality of respective select pairs of the magnetometers according to the equations:

$$\frac{\Delta B_{xyz}}{\Delta y} = \begin{pmatrix} \frac{B_{x_{S1}} - B_{x_{S2}}}{z_{S1-S2}} & \frac{B_{x_{S1}} - B_{x_{S3}}}{z_{S1-S3}} & \frac{B_{x_{S2}} - B_{x_{S3}}}{z_{S2-S3}} \\ \frac{B_{y_{S1}} - B_{y_{S2}}}{z_{S1-S2}} & \frac{B_{y_{S1}} - B_{y_{S3}}}{z_{S1-S3}} & \frac{B_{y_{S2}} - B_{y_{S3}}}{z_{S2-S3}} \\ \frac{B_{z_{S1}} - B_{z_{S2}}}{z_{S1-S2}} & \frac{B_{z_{S1}} - B_{z_{S3}}}{z_{S1-S3}} & \frac{B_{z_{S2}} - B_{z_{S3}}}{z_{S1-S3}} \end{pmatrix}$$

and $$\frac{\Delta B_{xyz}}{\Delta z} = \begin{pmatrix} \frac{B_{x_{S2}} - B_{x_{S5}}}{z_{S2-S5}} & \frac{B_{x_{S2}} - B_{x_{S6}}}{z_{S2-S6}} & \frac{B_{x_{S5}} - B_{x_{S6}}}{z_{S5-S6}} \\ \frac{B_{y_{S2}} - B_{y_{S5}}}{z_{S1-S5}} & \frac{B_{y_{S2}} - B_{y_{S6}}}{z_{S2-S6}} & \frac{B_{y_{S5}} - B_{y_{S6}}}{z_{S5-S6}} \\ \frac{B_{z_{S2}} - B_{z_{S5}}}{z_{S2-S5}} & \frac{B_{z_{S2}} - B_{z_{S6}}}{z_{S2-S6}} & \frac{B_{z_{S5}} - B_{z_{S6}}}{z_{S5-S6}} \end{pmatrix}$$

where S1, S2 and S3 represent three magnetometers of the at least three magnetometers disposed along the first axis, S2, S5 and S6 represent three magnetometers of the at least three magnetometers disposed along the second axis, $\Delta y$ represents distance along the first axis and $\Delta z$ represents distance along the second axis and $B_x$ represents strength of an x-axis magnetic field, $B_y$ represents strength of a y-axis magnetic field and $B_z$ represents strength of a z-axis magnetic field as measured by a respective one of the magnetometers S1, S2, S3, S5 and S6.

34. The system of claim 32, wherein:
the plurality of magnetometers is arranged in a three-dimensional array, wherein at least two magnetometers of the plurality of magnetometers are mutually spaced apart and disposed within the array along the x axis; and
the data processor is further configured to calculate, for each scan position of the plurality of scan positions, respective differences between a plurality of respective select pairs of the magnetometers along the x axis.

35. The system of claim 34, wherein the data processor is configured to calculate the respective differences between the plurality of respective select pairs of the magnetometers according to the equations:

$$\frac{\Delta B_{xyz}}{\Delta y} = \begin{pmatrix} \frac{B_{x_{S1}} - B_{x_{S2}}}{z_{S1-S2}} & \frac{B_{x_{S1}} - B_{x_{S3}}}{z_{S1-S3}} & \frac{B_{x_{S2}} - B_{x_{S3}}}{z_{S2-S3}} \\ \frac{B_{y_{S1}} - B_{y_{S2}}}{z_{S1-S2}} & \frac{B_{y_{S1}} - B_{y_{S3}}}{z_{S1-S3}} & \frac{B_{y_{S2}} - B_{y_{S3}}}{z_{S2-S3}} \\ \frac{B_{z_{S1}} - B_{z_{S2}}}{z_{S1-S2}} & \frac{B_{z_{S1}} - B_{z_{S3}}}{z_{S1-S3}} & \frac{B_{z_{S2}} - B_{z_{S3}}}{z_{S1-S3}} \end{pmatrix}$$

and $$\frac{\Delta B_{xyz}}{\Delta y} = \begin{pmatrix} \frac{B_{x_{S2}} - B_{x_{S5}}}{z_{S2-S5}} & \frac{B_{x_{S2}} - B_{x_{S6}}}{z_{S2-S6}} & \frac{B_{x_{S5}} - B_{x_{S6}}}{z_{S5-S6}} \\ \frac{B_{y_{S2}} - B_{y_{S5}}}{z_{S1-S5}} & \frac{B_{y_{S2}} - B_{y_{S6}}}{z_{S2-S6}} & \frac{B_{y_{S5}} - B_{y_{S6}}}{z_{S5-S6}} \\ \frac{B_{z_{S2}} - B_{z_{S5}}}{z_{S2-S5}} & \frac{B_{z_{S2}} - B_{z_{S6}}}{z_{S2-S6}} & \frac{B_{z_{S5}} - B_{z_{S6}}}{z_{S5-S6}} \end{pmatrix}$$

and $$\frac{\Delta B_{xyz}}{\Delta x} = \begin{pmatrix} B_{x_{S2}} - B_{x_{S4}} \\ B_{y_{S2}} - B_{y_{S4}} \\ B_{z_{S2}} - B_{z_{S4}} \end{pmatrix} \Big/ x_{S2-S4}$$

where S1, S2 and S3 represent three magnetometers of the at least three magnetometers disposed along the y axis, S2, S5 and S6 represent three magnetometers of the at least three magnetometers disposed along the z axis, S2 and S4 represent two magnetometers of the at least two magnetometers disposed along the x axis, $\Delta y$ represents distance along the first axis, $\Delta z$ represents distance along the second axis and $\Delta x$ represents distance along the x axis and $B_x$ represents strength of an x-axis magnetic field, $B_y$ represents strength of a y-axis magnetic field and $B_z$ represents strength of a z-axis magnetic field as measured by a respective one of the magnetometers S1, S2, S3, S4, S5 and S6.

36. The system of claim 20, wherein the data processor is configured to compare the respective differences between the plurality of respective select pairs of the magnetometers with the data representing the deterministic physics-based model of magnetic fields for missing metal using a sliding window.

37. The system of claim 20, wherein the differences comprise at least one numeric that is derived from magnetic field data measured by at least one magnetometer of the plurality of magnetometers, the numeric being chosen from the group of numerics consisting of: Fourier, Wavelet, magnetic field gradients, gradient Fourier transform, wavelet transform, $2^{nd}$ derivative matrices, Hessians and fractal dimension.

* * * * *